(12) United States Patent
Fujii et al.

(10) Patent No.: US 6,890,746 B1
(45) Date of Patent: May 10, 2005

(54) GENE PARTICIPATING IN THE PRODUCTION OF HOMO-GLUTAMIC ACID AND UTILIZATION THEREOF

(75) Inventors: Tadashi Fujii, Fujisawa (JP); Takao Narita, Zama (JP); Kuniho Nakata, Fujisawa (JP); Hitosi Agematu, Hadano (JP); Hiroshi Tsunekawa, Fujisawa (JP); Kunio Isshiki, Zama (JP); Takeo Yoshioka, Ayase (JP)

(73) Assignee: Mercian Corporation, Tokyo (JP)

( * ) Notice: Subject to any disclaimer, the term of this patent is extended or adjusted under 35 U.S.C. 154(b) by 0 days.

(21) Appl. No.: 09/762,230

(22) PCT Filed: Aug. 4, 1999

(86) PCT No.: PCT/JP99/04197
§ 371 (c)(1),
(2), (4) Date: Feb. 5, 2001

(87) PCT Pub. No.: WO00/08170
PCT Pub. Date: Feb. 17, 2000

(30) Foreign Application Priority Data

Aug. 5, 1998 (JP) ............................................. 10-232382
Jun. 28, 1999 (JP) ............................................. 11-182362

(51) Int. Cl.$^7$ ................................................ C12N 9/02
(52) U.S. Cl. .................... 435/189; 435/183; 435/252.3; 435/252.33; 435/320.1; 536/23.1; 536/23.2
(58) Field of Search ................................. 435/183, 189, 435/252.3, 252.33, 320.1; 536/23.1, 23.2

(56) References Cited

FOREIGN PATENT DOCUMENTS

WO 96/31616 10/1996

OTHER PUBLICATIONS

Attwood et al. Which craft is best in bioinformatics? Comput. Chem. 2001, vol. 25(4), pp. 329–339.*
Ponting, C.P. Issues in predicting protein function from sequence. Brief. Bioinform. Mar. 2001, vol. 2(1), pp. 19–29.*

T. Yagi et al., "L–Lysine: 2–Oxoglutarate 6–Aminotransferase", J. Biochem. (1980), vol. 87, No. 5, pp. 1395–1402.
T. Yagi et al., "A Novel Purification Procedure of L–Lysine 6–Aminotransferase from Flavobacterium Lutescence", Biochem., Biophys. Acta. (1980), vol. 614, No. 1, pp. 63–70.
J.R. Coque et al., "A Gene Encoding Lysine 6–Aminotransferase, Which Forms the β–Lactam Precursor α–Aminoadipic Acid, is Located in the Cluster of Cephamycin Biosynthetic Genes in Nocardia Lactamdurans", J. Bioteriol. (1991), vol. 173, No. 19, pp. 6258–6264.
K. Madduri et al., "Cloning of Location of a Gene Governing Lysine ε–Aminotransferase, an Enzyme Initialing β–Lactum Biosysthesis in Streptomyces spp.", J. Bioteriol. (1991), vol. 173, pp. 985–988.
J.F. Martin et al., "Genes for β–Lactum Antibiotic Biosynthesis", Antonie van Leeuwenhoek (1995), vol. 181, No. 2, pp. 181–200.
A.L. Leitao et al., "Inducing Effect of Diamines on Transcription of the Cephamycin C Genes from the lat and pcbAB Promoters in Nocardia Lactamdurans" J. Bacteriol. (Apr. 1999,), vol. 181, No. 8, pp. 2379–2384.
J.P. Francisco et al., "The pcd Gene Encoding Piperideine–6–Carboxylate dehydrogenase Involved in Biosynthesis of α–Aminoadipic Acid is Located in the Cephamycin Cluster of Streptomyces Clavuligerus", J. Bacteriol. (Sep. 1998,) vol. 180, No. 17, pp. 4753–4756.
L.F. Juan et al., "Δ–1–Piperideine–6–carboxylate dehydrogenease, a new enzyme that forms α–aminoadipate in *Streptomyces clavuligerus* and other cephamycin c–producing actinomycetes", Biochem. J. (1997), vol. 327, No. 1, pp. 59–64.

* cited by examiner

*Primary Examiner*—Tekchand Saidha
*Assistant Examiner*—Christian L. Fronda
(74) *Attorney, Agent, or Firm*—Wenderoth, Lind & Ponack, L.L.P.

(57) ABSTRACT

Provided are an isolated gene capable of participating in the production of L-homoglutamic acid, and a production system of L-homoglutamic acid by using this gene. The gene is derived from the genome of *Flavobacterium lutescens*.

15 Claims, 7 Drawing Sheets

SEQUENCE LISTING

<160> NUMBER OF SEQ ID NOS: 10

<210> SEQ ID NO 1
<211> LENGTH: 2663
<212> TYPE: DNA
<213> ORGANISM: Flavobacterium lutescens
<220> FEATURE:
<221> NAME/KEY: CDS
<222> LOCATION: (801)..(2276)

<400> SEQUENCE: 1

```
cccgggtgtc attgaatacc agcaggtcgc caggttgcag cagctggtcc agatcgcgca      60
cctggcgatc ctccagcgca gccggtgccg gcggcaccag cagcaggcgg ctggccgaac     120
gctccggcag cggcgcctgg gcaatcagtt cgggaggcag gtggtaggca aaatcggact     180
tcttcaacgc cggcagctcg atacaacggg ggcgtcagtt tacgcccctg taccgcctgt     240
gccctcaccg ctcgaacttg gtgcccagga tcaccgccgt ggtggtgcgc tcgaccccat     300
cagtggcgcc gatggcatcg gtcagctcgt ccatcgccgc cacgccatcg acggcggcca     360
tcgccaccag gtcatgcgcg ccactgaccg aatgcaggct gcgcaccgca gcaatggcct     420
gcagcgcccg cacgaccgcc ggcatttctc tcggcatcac ggtgatggag atatgcgcgc     480
ggacctgctg gcgctccatc gcctggccaa ggcgcacggt gtagccggcg attattccgc     540
```

```
                                                              -continued tgtgctgcag ccgctcgatc cggctctgca ccgtggtccg cgacaccccg agccggcgcg    600
ccagcgccgc ggtcgaggcg cgcgcatcct cacgcaacag gtcaagcaac tgtgcatccg    660
cctgggaaat ggtcactttg tcgaaaacct ttcgtcaatc cgccgaaacc ggccattgat    720
ttgagcagat tcgcactgcc atttgtagtg cgttaacggt tacaactaac actagacaca    780
atcagcacgg attcagcatg tcc ctt ctt gcc ccg ctc gcc ccg ctc cgc gcc    833
                      Ser Leu Leu Ala Pro Leu Ala Pro Leu Arg Ala
                        1               5                  10 cat gcc ggc acc cgc ctt acc cag ggc ctg tct gac ccg cag gtc gag      881
His Ala Gly Thr Arg Leu Thr Gln Gly Leu Ser Asp Pro Gln Val Glu
            15                  20                  25 cag ctg gcc gcc aac cac cct gac ctg cgc gcc gcc atc gac gcc gct      929
Gln Leu Ala Ala Asn His Pro Asp Leu Arg Ala Ala Ile Asp Ala Ala
         30                  35                  40 gcc gac gaa tac gcg cgc atc aaa ccg cag gcc gcg gca ttg ctg gac      977
Ala Asp Glu Tyr Ala Arg Ile Lys Pro Gln Ala Ala Ala Leu Leu Asp
     45                  50                  55 ctg gat gaa agc gcg cag atc gcc gcc gtg cag gat ggc ttc gtc aac     1025
Leu Asp Glu Ser Ala Gln Ile Ala Ala Val Gln Asp Gly Phe Val Asn
 60                  65                  70                  75 ttc tat gcc gat gat gcg gtg gtg ccc tat atc gcc ctg gcc gcc cgc     1073
Phe Tyr Ala Asp Asp Ala Val Val Pro Tyr Ile Ala Leu Ala Ala Arg
                 80                  85                  90 ggg ccg tgg gtg gtc agc ctg aag ggc gcg gtg ctg tat gac gcc ggc     1121
Gly Pro Trp Val Val Ser Leu Lys Gly Ala Val Leu Tyr Asp Ala Gly
             95                 100                 105 ggc tac ggc atg ctc ggc ttc ggc cat acc ccg gcc gat atc ctg gag     1169
Gly Tyr Gly Met Leu Gly Phe Gly His Thr Pro Ala Asp Ile Leu Glu
         110                 115                 120 gcg gtc ggc aag ccg cag gtg atg gcc aac atc atg act ccc tcg ctg     1217
Ala Val Gly Lys Pro Gln Val Met Ala Asn Ile Met Thr Pro Ser Leu
     125                 130                 135 gcc cag ggc cgc ttc att gcc gca atg cgc cgc gaa atc ggc cat acc     1265
Ala Gln Gly Arg Phe Ile Ala Ala Met Arg Arg Glu Ile Gly His Thr
140                 145                 150                 155 cgc ggc ggc tgc ccg ttc tcg cac ttc atg tgc ctg aac tcc ggc tcc     1313
Arg Gly Gly Cys Pro Phe Ser His Phe Met Cys Leu Asn Ser Gly Ser
                 160                 165                 170 gaa gcg gtc ggg ctg gcc gcg cgc atc gcc gac atc aac gcc aag ctg     1361
Glu Ala Val Gly Leu Ala Ala Arg Ile Ala Asp Ile Asn Ala Lys Leu
             175                 180                 185 atg acc gac ccg ggc gcc cgg cat gcc ggc gcc acg atc aag cgc gtg     1409
Met Thr Asp Pro Gly Ala Arg His Ala Gly Ala Thr Ile Lys Arg Val
         190                 195                 200 gtg atc aag ggc agt ttc cac ggc cgt acc gac cgt ccg gcg ctg tat     1457
Val Ile Lys Gly Ser Phe His Gly Arg Thr Asp Arg Pro Ala Leu Tyr
     205                 210                 215 tcc gat tcc acc cgc aag gcc tac gat gcg cat ctg gcc agc tac cgc     1505
Ser Asp Ser Thr Arg Lys Ala Tyr Asp Ala His Leu Ala Ser Tyr Arg
220                 225                 230                 235 gac gag cac agc gtc att gcc atc gcc ccg tat gac cag cag gcc ctg     1553
Asp Glu His Ser Val Ile Ala Ile Ala Pro Tyr Asp Gln Gln Ala Leu
                 240                 245                 250 cgc cag gtg ttt gcc gat gcc cag gcc aac cac tgg ttc atc gag gcg     1601
Arg Gln Val Phe Ala Asp Ala Gln Ala Asn His Trp Phe Ile Glu Ala
             255                 260                 265 gtg ttc ctg gag ccg gtg atg ggc gaa ggc gac ccg ggc cgt gcg gtg     1649
Val Phe Leu Glu Pro Val Met Gly Glu Gly Asp Pro Gly Arg Ala Val
         270                 275                 280
```

```
                                                                    -continued ccg gtg gac ttc tac cgc ctg gcc cgt gag ctg acc cgc gaa cac ggc      1697
Pro Val Asp Phe Tyr Arg Leu Ala Arg Glu Leu Thr Arg Glu His Gly
    285                 290                 295 agc ctg ctg ctg atc gat tcg atc cag gcc gcg ctg cgc gtg cac ggc      1745
Ser Leu Leu Leu Ile Asp Ser Ile Gln Ala Ala Leu Arg Val His Gly
300                 305                 310                 315 acc ctg tcc ttc gtc gac tac ccc ggc cac cag gag ctg gag gca ccg      1793
Thr Leu Ser Phe Val Asp Tyr Pro Gly His Gln Glu Leu Glu Ala Pro
                320                 325                 330 gac atg gag acc tac tcc aag gcc ctg aac ggc gcc cag ttc ccg ctg      1841
Asp Met Glu Thr Tyr Ser Lys Ala Leu Asn Gly Ala Gln Phe Pro Leu
            335                 340                 345 tcg gta gtg gcc gtg acc gag cac gcc gcc gcg ctg tac cgc aag ggc      1889
Ser Val Val Ala Val Thr Glu His Ala Ala Ala Leu Tyr Arg Lys Gly
        350                 355                 360 gtg tac ggc aac acc atg acc acc aac ccg cgg gcg ctg gac gtg gcc      1937
Val Tyr Gly Asn Thr Met Thr Thr Asn Pro Arg Ala Leu Asp Val Ala
    365                 370                 375 tgc gcc acc ctg gca cgc ctg gat gag ccg gtc cgc aac aat atc cgc      1985
Cys Ala Thr Leu Ala Arg Leu Asp Glu Pro Val Arg Asn Asn Ile Arg
380                 385                 390                 395 ctg cgt ggc cag cag gcg atg cag aag ctg gaa gca ttg aag gaa cgg      2033
Leu Arg Gly Gln Gln Ala Met Gln Lys Leu Glu Ala Leu Lys Glu Arg
                400                 405                 410 ctg ggg ggc gcg atc acc aag gtg cag ggc acc ggc ctg ctg ttc tcc      2081
Leu Gly Gly Ala Ile Thr Lys Val Gln Gly Thr Gly Leu Leu Phe Ser
            415                 420                 425 tgc gag ctg gcc ccg cag tac aag tgc tac ggg gcc ggc tcc acc gag      2129
Cys Glu Leu Ala Pro Gln Tyr Lys Cys Tyr Gly Ala Gly Ser Thr Glu
        430                 435                 440 gag tgg ctg cgc atg cac ggg gtc aat gtg atc cac ggc ggc gag aat      2177
Glu Trp Leu Arg Met His Gly Val Asn Val Ile His Gly Gly Glu Asn
    445                 450                 455 tcg ctg cgc ttc acc ccg cac ttc ggc atg gac gag gcc gaa ctg gac      2225
Ser Leu Arg Phe Thr Pro His Phe Gly Met Asp Glu Ala Glu Leu Asp
460                 465                 470                 475 ctg ctg gtg gag atg gtc ggg cgt gcg ctg gtc gaa ggc cca cgc cgg      2273
Leu Leu Val Glu Met Val Gly Arg Ala Leu Val Glu Gly Pro Arg Arg
                480                 485                 490 gcc tga tccgcacccg caggacggaa ggcacgagcc caccgtgagg cgggctcttt gc    2331
Ala tgcccggcac cagcggcaac aggccgcgct gtcaccggcc aggcggggcg ccggcagtgg    2391
gtttcagccg caggggtccg ccctgccagc gcctgcggcg gggcacaggc ttgcgggcat    2451
tgcggcctct gccacgggca cgcagccgga gatcaggctg acaaggggc tgccccgggt    2511 ggcagtacac gaccagccag ttgactgccg gtatttgctt gatcagcgct gcatccagaa    2571
cagcaccatc ggttgcgtga ctgacgcgcc gctggccgtt gcgggacagc agcctttgcg    2631
tcacacgtgg cccgcacctg cctgcactgc ag                                   2663

<210> SEQ ID NO 2
<211> LENGTH: 6357
<212> TYPE: DNA
<213> ORGANISM: Flavobacterium lutescens
<220> FEATURE:
<221> NAME/KEY: CDS
<222> LOCATION: (2855)..(4387)
```

-continued

```
<400> SEQUENCE: 2
ggatcgggcc actgggctca ctgctggacg caatccgagt gccgggatgg ctcgggttga      60
aggtgttgcg gatcacgatc ggcatctgcc gggcgatggc cgggctcatc gtctgcgggt     120
gcaccacctt ggcgccgaaa taggccagtt cgcaggcctc gtcatagctg agcgtggcca     180
gggtcaccgc ctcgggcacc acccgcgggt cggccgacag cacaccgtcg acatcggtcc     240
agatgtgcag ctcggccgcc tcgaacagcg cggcaaagat cgccccggaa taatcgctgc     300
cgttgcggcc cagggtggtg atcctgccct ggccatcacg ggcgacaaaa ccggtgacca     360
ccacccgcga ctgcgggttg tccacacgcc aggcggccag gttggccgca ctgcgttccc     420
agtcgacgct gaccccagc tcgccgtgtg cgaccaccag cacatcgcgg gcatcgagca      480
ccgcgcaggg gtgccgagc cggttgaaat agcggcccag cagctgggcc gagaacacct      540
cgcccagccc ctgcacccctt tcaagcacct cctcgggcag gccgccgatc accgccagcg    600
cttccagcaa cccggccagc ttgtcaaagc gtccatccag ccactgcagc aggtcggcag     660
aatcctcgcc cagcagttcg gtggccgctt catggtggcg ctggcgcagg gcctgccagg     720
catcacgcca gcgcggctga ccgtgggcgg ccagggtagc cagctcgatc aaggcatcgg     780 tgacacccctt catcgccgag accaccacca cctgggtggg ttccgggcgc tgcagcagca    840
actcggcgac atggcggtag cgctgcgccg aggccaccga ggtgccgccg aacttgtggg     900
cgatgacctg ggcatcgggc gcgggagcgg gagcgggtgc agcggcaggc gatgacatca     960
caacagacct ctgggggttga ggcccggcac cgcaggttgc gaagtcccgc aacctggtcg    1020
gtgcggggcc gttgttttcg ggggttagac gaatacgacg ggccgcacca gccaagtggt    1080
ggtggtaatg atggtcatgc cggtgacgcc agcaggcgcc agcagggcgg cagtggaatc    1140
aacggtggcg cggcagatcg acatgcagcg agcagaccgc acagcgcctg ctgctgtcaa    1200
ctgttgcatt gcaaaataat tttccgcgca tcatcggcga acatgcaccg atttggttgc    1260
aaatgtgatc gtcagcgatc ttctgtcaaa cccgcggat caagcggcca cagccgctgc     1320
ggcagccgcg gaccaccgcg cgccgatgcc agcgccgggc ggcagagcaa gccgccagcg    1380
caaccggcca ttaccgcggc caggcgccgg gcctgcgcgg ctcaaccgtg gatttttttcc   1440 cagcgggcgt gggcctgcgc ggccagcacc accccgccga ccaacagcgc aatggccagc    1500
agctccagca gggtcgggcc acgctgctgc agatgaagc cataaagcaa cgcgaacagg     1560
gtttcaaaca cgatcagctg cccgcccagg ctcagcggca ggctgcgcgt ggcccggttc    1620
cagcaggcat tgcccagcac cgaggcaccg acggccagca gcgcacagat gccggcaaag    1680
tgcagccact ggccctggct ctgcccgagc ggccccagcc acagcgccag cggcagcaac    1740
agcacggcga tggcccctgt ggccaccccg gtcaacaacg accaggcatg cccggacagg    1800
tgcggatagc gccgcatcca caccacattg gcgatcgagt agccactcca ggcggccagc    1860
gcggccagcg cgcagagcag gcccagcacc cgctgaccga tgtccttgcc agcatcgccc    1920
gccgcgcccg cgccgtggcc gagtgcagcc caggccacca gcagcgagcc cagcacacac    1980
aggcacagcc ccggtgccag ctgacgcaac ggcagggcc ttggccgccg cgcatccacc     2040
gccgccacca ccaccggcac catgcccacg atcagcgcgg ccgccgcacc gccagcccag    2100
tgcacggcca tcgccagaaa cacgaaatag accaggttgc cgagcaggct cagcccggcc    2160
agggccagcc aggcgcggcg atcgacctgc gcacgcagcg ccggccacaa cggcagcagc    2220
aacgcacagg ccaccgcacc gtacagcagg tagcggccca cggccagctg cagcgcagaa    2280
aatgcggtgg tcaaggccgg cgccaggaac accatgcccc acagggcacc ggcgagcacg    2340
```

-continued

```
ccgttgaaca gtccccacgc ggtctggttg ttgcgctgga tcacgctgca aggccctgca      2400
atgaacaaca ggccggggcg gcgcagcgca tgggcgctgg cagctctccg acctgtgcaa      2460
aggtggtggc cccgacacga ttcgaacgtg cgacctgtcc cttaggaggg gaccgctcta      2520
tccagctgag ctacggagcc atgaggccgg cgattctagc atccgctctc cgttcacggc      2580
catcgcccgc agccgcagtt cacagtgcag ggcaaccgca gcaagccccc gccccgctgc      2640
aaccctcgcg cccgcgcgca acgtgaccgg cgccgcggca ggcccggccc ccacggccac      2700
tggcgccggt tccgcaccac gccaccggca acacgccccc agccctgccc aacgtggtgt      2760
ttcagcgctc tgttaagatg gcatgccacg atgccacctc cccccggacg cgccgcgggt      2820
gcgtgacctt ttcgtaacgt aatctggagt ttcc atg tcg ttt gaa ctg ctc aag      2875
                                      Met Ser Phe Glu Leu Leu Lys
                                       1               5 gcc tta ggg ctg gac gcc acc aat tcc ggc acc tac ctg ggt gat gga        2923
Ala Leu Gly Leu Asp Ala Thr Asn Ser Gly Thr Tyr Leu Gly Asp Gly
         10                  15                  20 gaa tgg tcc agc gct acc ggt gcc ggg acc atc agc ccg cgc aac ccg        2971
Glu Trp Ser Ser Ala Thr Gly Ala Gly Thr Ile Ser Pro Arg Asn Pro
     25                  30                  35 acc acc ggc gag gtc att gcc cag gtc cag gcc acc acc gag gcg gac        3019
Thr Thr Gly Glu Val Ile Ala Gln Val Gln Ala Thr Thr Glu Ala Asp
 40                  45                  50                  55 tac gaa acc atc ctg gcc cgc gcc cag cag gcc ttc aag gtc tgg cgc        3067
Tyr Glu Thr Ile Leu Ala Arg Ala Gln Gln Ala Phe Lys Val Trp Arg
             60                  65                  70 acc acc ccg gca ccg cgc cgc ggc gag gcc atc cgc ctg tgt ggc gag        3115
Thr Thr Pro Ala Pro Arg Arg Gly Glu Ala Ile Arg Leu Cys Gly Glu
         75                  80                  85 gcc ctg cgc cgc cac aag gac gcg ctg ggt tcg ctg gtc gcg ctg gaa        3163
Ala Leu Arg Arg His Lys Asp Ala Leu Gly Ser Leu Val Ala Leu Glu
     90                  95                 100 atg ggc aag tcc aag ccg gaa ggc gac ggc gaa gtc cag gaa atg atc        3211
Met Gly Lys Ser Lys Pro Glu Gly Asp Gly Glu Val Gln Glu Met Ile
105                 110                 115 gac atc gcc gac ttt gcc gtc ggc cag agc cgc atg ctg tat ggc tac        3259
Asp Ile Ala Asp Phe Ala Val Gly Gln Ser Arg Met Leu Tyr Gly Tyr
120                 125                 130                 135 acc atg cac agc gag cgc ccc ggc cac cgc atg tac gag cag tac cag        3307
Thr Met His Ser Glu Arg Pro Gly His Arg Met Tyr Glu Gln Tyr Gln
             140                 145                 150 ccg ctg ggc atc gtc ggc atc atc tcg gcc ttc aac ttc ccg gtc gcg        3355
Pro Leu Gly Ile Val Gly Ile Ile Ser Ala Phe Asn Phe Pro Val Ala
         155                 160                 165 gtc tgg gcc tgg aac agc ttc ctg gcc gcg atc tgt ggt gat gtc tgc        3403
Val Trp Ala Trp Asn Ser Phe Leu Ala Ala Ile Cys Gly Asp Val Cys
     170                 175                 180 atc tgg aag ccg tcc aac aag acc ccg ctg acc gcg atc gcg tcc atg        3451
Ile Trp Lys Pro Ser Asn Lys Thr Pro Leu Thr Ala Ile Ala Ser Met
185                 190                 195 cgc atc tgc aac gaa gca ctg cgc gaa ggc ggc ttc ccg gac atc ttc        3499
Arg Ile Cys Asn Glu Ala Leu Arg Glu Gly Gly Phe Pro Asp Ile Phe
200                 205                 210                 215 ttc ctg atc aac gac gcc ggc acc gcg ttg tcg gag aag ctg gtc gag        3547
Phe Leu Ile Asn Asp Ala Gly Thr Ala Leu Ser Glu Lys Leu Val Glu
             220                 225                 230 gac aag cgc gtg ccg ctg atc tcc ttc acc ggc tcg acc cag gtc ggg        3595
Asp Lys Arg Val Pro Leu Ile Ser Phe Thr Gly Ser Thr Gln Val Gly
         235                 240                 245
```

-continued

| | |
|---|---|
| cgc atc gtc aac cag aag gtc gcc gcc cgc ctg ggc cgc tgc ctg ctc<br>Arg Ile Val Asn Gln Lys Val Ala Ala Arg Leu Gly Arg Cys Leu Leu<br>250                             255                           260 | 3643 |
| gag ctg ggc ggc aac aac gcg atc atc ctg gac gaa acc gcc gac ctg<br>Glu Leu Gly Gly Asn Asn Ala Ile Ile Leu Asp Glu Thr Ala Asp Leu<br>265                             270                        275 | 3691 |
| aag ctg gcc gtg ccg ggc atc gtc ttc ggc gcc gtc ggc acc gcc ggc<br>Lys Leu Ala Val Pro Gly Ile Val Phe Gly Ala Val Gly Thr Ala Gly<br>280                         285                        290                        295 | 3739 |
| cag cgc tgc acc acc acc cgc cgc ctg atc gtg cac gaa tcg atc tac<br>Gln Arg Cys Thr Thr Thr Arg Arg Leu Ile Val His Glu Ser Ile Tyr<br>                     300                        305                        310 | 3787 |
| gac aac gtg ctg gcc acc ttg atc aag gcc tac aag cag gtc gaa ggc<br>Asp Asn Val Leu Ala Thr Leu Ile Lys Ala Tyr Lys Gln Val Glu Gly<br>315                           320                        325 | 3835 |
| aag atc ggc gat ccg ctg gat gcc gcc aac ctg atg ggc ccg ctc aac<br>Lys Ile Gly Asp Pro Leu Asp Ala Ala Asn Leu Met Gly Pro Leu Asn<br>                     330                        335                        340 | 3883 |
| agc ccc gaa gcg gtg cag cag ttc ctg gcc tcg atc gag aaa gcc aag<br>Ser Pro Glu Ala Val Gln Gln Phe Leu Ala Ser Ile Glu Lys Ala Lys<br>345                           350                        355 | 3931 |
| gcc gct ggc ggc acc gtt caa acc ggt ggt acc gcg atc gac cgc ccg<br>Ala Ala Gly Gly Thr Val Gln Thr Gly Gly Thr Ala Ile Asp Arg Pro<br>360                         365                        370                        375 | 3979 |
| ggc aac ttc gtg ctg ccg gcc atc gtc acc ggc ctg aag aac agc gat<br>Gly Asn Phe Val Leu Pro Ala Ile Val Thr Gly Leu Lys Asn Ser Asp<br>                     380                        385                        390 | 4027 |
| gag gtg gtc cag cac gag acc ttc gcc ccg atc ctg tac gta atg aag<br>Glu Val Val Gln His Glu Thr Phe Ala Pro Ile Leu Tyr Val Met Lys<br>395                           400                        405 | 4075 |
| tac tcc acc ctg gac gaa gcc atc gag atg cag aac ggc gtg ccg cag<br>Tyr Ser Thr Leu Asp Glu Ala Ile Glu Met Gln Asn Gly Val Pro Gln<br>                     410                        415                        420 | 4123 |
| ggc ctg tcc tcg tcg atc ttc acc acg aac ctg aag gca gcc gag aag<br>Gly Leu Ser Ser Ser Ile Phe Thr Thr Asn Leu Lys Ala Ala Glu Lys<br>425                           430                        435 | 4171 |
| ttc ctg tcg gcg gcc ggc agc gac tgc ggc att gcc aac gtc aac atc<br>Phe Leu Ser Ala Ala Gly Ser Asp Cys Gly Ile Ala Asn Val Asn Ile<br>440                         445                        450                        455 | 4219 |
| ggc act tcc ggt gcc gag atc ggc ggc gcc ttc ggt ggc gag aag gaa<br>Gly Thr Ser Gly Ala Glu Ile Gly Gly Ala Phe Gly Gly Glu Lys Glu<br>                     460                        465                        470 | 4267 |
| acc ggc ggt ggc cgt gag tcc ggc tcg gat gcg tgg aag gtc tac atg<br>Thr Gly Gly Gly Arg Glu Ser Gly Ser Asp Ala Trp Lys Val Tyr Met<br>475                           480                        485 | 4315 |
| cgc cgc cag acc aac acc atc aac tac tcc gac tcg ctg ccg ctg gcc<br>Arg Arg Gln Thr Asn Thr Ile Asn Tyr Ser Asp Ser Leu Pro Leu Ala<br>                     490                        495                        500 | 4363 |
| cag ggc atc aag ttc gac ctg taa gccgctcgcc acggcccgcc ttccccggaa<br>Gln Gly Ile Lys Phe Asp Leu<br>505                     510 | 4417 |
| gcaggccgtg gctgttgcac cagccagagg agtgactgca tgactgcaat tgaatcgact | 4477 |
| gccgcacgca ccaccaacac ttgcgccatc ctgtcgctgg tactggcact gctgggctgg | 4537 |
| aatcttttgc cggtgattgg ctttgtcggc gccatcatct gcggccgcat cgcccagcgc | 4597 |
| cagctcaagc agcccggcaa tacccaggac ggtcacggcc tggcaagggc gggcatctgg | 4657 |
| atcagttgga tcagcctgat cctggttgcg ctgctgatcg gcgtcgtgat cccgtggttg | 4717 |
| accgccccga tcacgatcaa cctgcccgtt tccacctgac cctcctccct gccagtcgcc | 4777 |

```
catgcgctga caggccaacc cgtttcctgc ctggaccaga ccatgctccc gcccgaccat    4837
ccggctccac catcgcccat tgccggcacc acaacctcga ccaatggcta tgcggtggcc    4897
tcgctggtga tgggcatcct tggctggtcg atgatcccgc tgttgggcag catcggcgcc    4957
atcgtgttcg ggcatctggc ccgggcgcag atccgtcgcc agccccagca gggcgatggc    5017
ctggcactgg ccgggctgat cctgggctgg atctcgattg cgctgtggat cctcgggatc    5077
ctggcgtttt tcctcttctt tggcgggctg gccatgctgc tcagcctgaa cgcctgaccc    5137
gagccttgcc gtatgtattc cctgctccgt cccgccctgt tctgcatgga tgccgagcgc    5197
gcccatggcg ccggcctgcg cgccctggat cttgcctacc gcagcggtac gctgggcctg    5257
ctggccagcc ggccagcacc gcttccaacc cgcgctttcg gcctggaatt ccccaacccg    5317
gtgggcctgg cggccggcct ggacaagaac ggcgagcata tcgatgcact gttcgcgctg    5377
ggctttggct atgtcgaaat cggcacggtg accccgcgcc cgcaggccgg caatccgcag    5437
ccacggctgt tccgcgtgcc cgagcacctg ggcgtgatca accgcatggg tttcaacaat    5497
gccggcgtcg atgcgctggt ggccaatgtg cgcgcggcac ggcgtgaccg cggcatcctc    5557
ggcatcaaca tcggcaagaa caaggacacc cccaacgagc tggcccatac cgattacctg    5617
acctgcctgg aaaaggtgta cgcgctggcc gactacatca ccgtcaacat ctcctcgccc    5677
aacaccgccg ggctgcgcga gctgcaggaa gaacaggccc tgcgcgagct ggtcagccgc    5737
ctgcgcgagg gccaggaaac cctggccgca cgccatggca gcgggtgcc gatgctggtc    5797 aaggtcgcgc cggacctgag cgatgccgat gtcgatgccg ccgcccgtgt gctggcagag    5857
ctgcaggtgg acggggtgat cgccaccaac accaccatcg cgcgcgtggg catggaaaac    5917
cacccactgg ccagcgaggc cggcggcctg tccggggcac cggtgatggc gcgctccacc    5977
gcggtgctgc gccgcctgcg cacccggctg ccggagtcga tcccgctgat cggcgtcggc    6037
ggcatctgtt ccggggctga tgcggcggcc aagatgagtg ccggcgcgac catggtgcag    6097
ctctacagcg ggctggttta ccgcggcccg gcactggtcg gcgaatgcgt cgaatcgatc    6157
cgccgccggc gcgaagcgcc ctccagcggg gtagcccatc tgtgagtacg ccgggctggc    6217
agctgcacca cgatgtcgca ctgcaatcaa tgaacaccttc cggggtagcg gccaccgcgc    6277
cgcgcctgct cgcgcgtgcac gacagccagg ccctgccggc ggcgctggcg cacccggaag    6337
tagccggaca gccgttgatc                                                 6357
```

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: DNA PRIMER

<400> SEQUENCE: 3
ttgatttgag cagattcgca ctgccattt                                          29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: DNA PRIMER

<400> SEQUENCE: 4
aaggttttcg acaaagtgac catttccca                                          29

```
<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: DNA PRIMER

<400> SEQUENCE: 5
ctggtaccgc tcgatccggc tctgcaccgt                                              30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: DNA PRIMER

<400> SEQUENCE: 6
ctggagctca ggcaggtgcg ggccacgtgt                                              30

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: N-terminus
      Amino Acid Sequence

<400> SEQUENCE: 7

Ser Leu Leu Ala Pro Leu Ala Pro Leu Arg Ala His Ala Gly Thr Arg Leu
1               5                   10                  15

Thr Gln Gly
        20

<210> SEQ ID NO 8
<211> LENGTH: 32
<212> TYPE: DNA
<213> ORGANISM: Artificial Sequence
<220> FEATURE:
<221> NAME/KEY: base
<222> LOCATION: (3)
<223> OTHER INFORMATION: y = t or c
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: base
<222> LOCATION: (11)
<223> OTHER INFORMATION: r = g or a
<220> FEATURE:
<221> NAME/KEY: modified_base
<222> LOCATION: (12)
<223> OTHER INFORMATION: i
<220> FEATURE:
<221> NAME/KEY: base
<222> LOCATION: (14)
<223> OTHER INFORMATION: k = g or t
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i
```

```
<220> FEATURE:
<221> NAME/KEY: modified_base
<222> LOCATION: (21)
<223> OTHER INFORMATION: i
<220> FEATURE:
<221> NAME/KEY: base
<222> LOCATION: (24)
<223> OTHER INFORMATION: r = g or a
<220> FEATURE:
<221> NAME/KEY: modified_base
<222> LOCATION: (27)
<223> OTHER INFORMATION: i
<220> FEATURE:
<221> NAME/KEY: modified_base
<222> LOCATION: (30)
<223> OTHER INFORMATION: i
<220> FEATURE:
<223> OTHER INFORMATION: Description of Artificial Sequence: DNA PRIMER

<400> SEQUENCE: 8
ccytgngtna rnckngtncc ngcrtgngcn cg                                  32

<210> SEQ ID NO 9
<211> LENGTH: 32
<212> TYPE: DNA
<213> ORGANISM: Artificial Sequence
<220> FEATURE:
<221> NAME/KEY: modified_base
<222> LOCATION: (3)
<223> OTHER INFORMATION: i
<220> FEATURE:
<221> NAME/KEY: base
<222> LOCATION: (6)
<223> OTHER INFORMATION: r = g or a
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: base
<222> LOCATION: (17)
<223> OTHER INFORMATION: r = g or a
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (21)
<223> OTHER INFORMATION: i
<220> FEATURE:
<221> NAME/KEY: modified_base
<222> LOCATION: (24)
<223> OTHER INFORMATION: i
<220> FEATURE:
<221> NAME/KEY: base
<222> LOCATION: (26)
<223> OTHER INFORMATION: r = g or a
<220> FEATURE:
<221> NAME/KEY: modified_base
<222> LOCATION: (27)
<223> OTHER INFORMATION: i
<220> FEATURE:
<221> NAME/KEY: modified_base
<222> LOCATION: (30)
<223> OTHER INFORMATION: i
<220> FEATURE:
<223> OTHER INFORMATION: Description of Artificial Sequence: DNA PRIMER
```

-continued

```
<400> SEQUENCE: 9
ccngcrtgng cncgnarngg ngcnarnggn gc                                    32

<210> SEQ ID NO 10
<211> LENGTH: 510
<212> TYPE: PRT
<213> ORGANISM: Flavobacterium lutescens

<400> SEQUENCE: 10
```

| | | | | | | | | | | | | | | |
|---|---|---|---|---|---|---|---|---|---|---|---|---|---|---|
| Met | Ser | Phe | Glu | Leu | Leu | Lys | Ala | Leu | Gly | Leu | Asp | Ala | Thr | Asn | Ser |
| 1 | | | | 5 | | | | | 10 | | | | | 15 | |
| Gly | Thr | Tyr | Leu | Gly | Asp | Gly | Glu | Trp | Ser | Ser | Ala | Thr | Gly | Ala | Gly |
| | | | 20 | | | | | 25 | | | | | 30 | | |
| Thr | Ile | Ser | Pro | Arg | Asn | Pro | Thr | Thr | Gly | Glu | Val | Ile | Ala | Gln | Val |
| | | | 35 | | | | | 40 | | | | | 45 | | |
| Gln | Ala | Thr | Thr | Glu | Ala | Asp | Tyr | Glu | Thr | Ile | Leu | Ala | Arg | Ala | Gln |
| | | 50 | | | | | 55 | | | | | 60 | | | |
| Gln | Ala | Phe | Lys | Val | Trp | Arg | Thr | Thr | Pro | Ala | Pro | Arg | Arg | Gly | Glu |
| 65 | | | | | 70 | | | | | 75 | | | | | 80 |
| Ala | Ile | Arg | Leu | Cys | Gly | Glu | Ala | Leu | Arg | Arg | His | Lys | Asp | Ala | Leu |
| | | | | 85 | | | | | 90 | | | | | 95 | |
| Gly | Ser | Leu | Val | Ala | Leu | Glu | Met | Gly | Lys | Ser | Lys | Pro | Glu | Gly | Asp |
| | | | 100 | | | | | 105 | | | | | 110 | | |
| Gly | Glu | Val | Gln | Glu | Met | Ile | Asp | Ile | Ala | Asp | Phe | Ala | Val | Gly | Gln |
| | | | 115 | | | | | 120 | | | | | 125 | | |
| Ser | Arg | Met | Leu | Tyr | Gly | Tyr | Thr | Met | His | Ser | Glu | Arg | Pro | Gly | His |
| | | 130 | | | | | 135 | | | | | 140 | | | |
| Arg | Met | Tyr | Glu | Gln | Tyr | Gln | Pro | Leu | Gly | Ile | Val | Gly | Ile | Ile | Ser |
| 145 | | | | | 150 | | | | | 155 | | | | | 160 |
| Ala | Phe | Asn | Phe | Pro | Val | Ala | Val | Trp | Ala | Trp | Asn | Ser | Phe | Leu | Ala |
| | | | | 165 | | | | | 170 | | | | | 175 | |
| Ala | Ile | Cys | Gly | Asp | Val | Cys | Ile | Trp | Lys | Pro | Ser | Asn | Lys | Thr | Pro |
| | | | 180 | | | | | 185 | | | | | 190 | | |
| Leu | Thr | Ala | Ile | Ala | Ser | Met | Arg | Ile | Cys | Asn | Glu | Ala | Leu | Arg | Glu |
| | | | 195 | | | | | 200 | | | | | 205 | | |
| Gly | Gly | Phe | Pro | Asp | Ile | Phe | Phe | Leu | Ile | Asn | Asp | Ala | Gly | Thr | Ala |
| | | 210 | | | | | 215 | | | | | 220 | | | |
| Leu | Ser | Glu | Lys | Leu | Val | Glu | Asp | Lys | Arg | Val | Pro | Leu | Ile | Ser | Phe |
| 225 | | | | | 230 | | | | | 235 | | | | | 240 |
| Thr | Gly | Ser | Thr | Gln | Val | Gly | Arg | Ile | Val | Asn | Gln | Lys | Val | Ala | Ala |
| | | | | 245 | | | | | 250 | | | | | 255 | |
| Arg | Leu | Gly | Arg | Cys | Leu | Leu | Glu | Leu | Gly | Gly | Asn | Asn | Ala | Ile | Ile |
| | | | 260 | | | | | 265 | | | | | 270 | | |
| Leu | Asp | Glu | Thr | Ala | Asp | Leu | Lys | Leu | Ala | Val | Pro | Gly | Ile | Val | Phe |
| | | | 275 | | | | | 280 | | | | | 285 | | |
| Gly | Ala | Val | Gly | Thr | Ala | Gly | Gln | Arg | Cys | Thr | Thr | Thr | Arg | Arg | Leu |
| | | 290 | | | | | 295 | | | | | 300 | | | |
| Ile | Val | His | Glu | Ser | Ile | Tyr | Asp | Asn | Val | Leu | Ala | Thr | Leu | Ile | Lys |
| 305 | | | | | 310 | | | | | 315 | | | | | 320 |
| Ala | Tyr | Lys | Gln | Val | Glu | Gly | Lys | Ile | Gly | Asp | Pro | Leu | Asp | Ala | Ala |
| | | | | 325 | | | | | 330 | | | | | 335 | |
| Asn | Leu | Met | Gly | Pro | Leu | Asn | Ser | Pro | Glu | Ala | Val | Gln | Gln | Phe | Leu |
| | | | 340 | | | | | 345 | | | | | 350 | | |

-continued

```
Ala Ser Ile Glu Lys Ala Lys Ala Ala Gly Gly Thr Val Gln Thr Gly
        355                 360                 365

Gly Thr Ala Ile Asp Arg Pro Gly Asn Phe Val Leu Pro Ala Ile Val
    370                 375                 380

Thr Gly Leu Lys Asn Ser Asp Glu Val Val Gln His Glu Thr Phe Ala
385                 390                 395                 400

Pro Ile Leu Tyr Val Met Lys Tyr Ser Thr Leu Asp Glu Ala Ile Glu
                405                 410                 415

Met Gln Asn Gly Val Pro Gln Gly Leu Ser Ser Ser Ile Phe Thr Thr
            420                 425                 430

Asn Leu Lys Ala Ala Glu Lys Phe Leu Ser Ala Ala Gly Ser Asp Cys
        435                 440                 445

Gly Ile Ala Asn Val Asn Ile Gly Thr Ser Gly Ala Glu Ile Gly Gly
    450                 455                 460

Ala Phe Gly Gly Glu Lys Glu Thr Gly Gly Arg Glu Ser Gly Ser
465                 470                 475                 480

Asp Ala Trp Lys Val Tyr Met Arg Arg Gln Thr Asn Thr Ile Asn Tyr
                485                 490                 495

Ser Asp Ser Leu Pro Leu Ala Gln Gly Ile Lys Phe Asp Leu
            500                 505                 510
```

GENE PARTICIPATING IN THE PRODUCTION OF HOMO-GLUTAMIC ACID AND UTILIZATION THEREOF

BACKGROUND OF THE INVENTION

1. Field of the Invention

This invention relates to gene manipulation, and more specifically, relates to a DNA containing a gene participating in the production of L-homoglutamic acid (also referred to as L-2-amino-adipic acid or L-α-aminoadipic acid), and a production system of L-homoglutamic acid (hereinafter, merely referred to as homoglutamic acid) using it.

2. Description of the Related Art

Homoglutamic acid is found widely in organisms such as plants including *Cholera vibrio* as a bacterium and corn (*Zea mays*), the embryos of frogs. Homoglutamic acid acts as an intermediate of lysine biosynthesis in fungi, etc. and as a precursor in biosynthesis of β-lactam antibiotics. Further, homoglutamic acid is also useful as a synthetic intermediate of various medicines including methotrexate derivatives (WO 92/09436).

Since preparation of homoglutamic acid by chemical synthesis needs optical resolution and multistage reaction, it is not a useful means from the aspect of costs. On the other hand, a process of preparing homoglutamic acid from L-lysine using a microorganism belonging to the genus *Agrobacterium, Klebsiella, Alcaligenes, Brevibacterium* or *Bacillus* is known (Japanese Laid-open Patent Publication No. 6-181787). Part of the present inventors also proposed a process of preparing homoglutamic acid from L-lysine using a microorganism belonging to the genus *Flavobacterium* (WO 96/31616). However, even in the process using such a microorganism, a process capable of preparing homoglutamic acid more efficiently is desired earnestly.

Thus, the present inventors aimed to reinforce the production system of homoglutamic acid in any of the above microorganisms, for example by gene manipulation. When a review of helpful information is made on the manipulation, for example, as part of researches of biosynthetic pathway of cephamycin C, are confirmed the presence of lysine-6-aminotransferase and L-Δ¹-piperidine-carboxylate dehydrogenase participating in conversion from L-lysine to α-amino-adipic acid (or homoglutamic acid) of *Streptomyces clavuligerus* as a cephamycin C-producing actinomycetes, and as to the former, the presence position of the gene encoding the enzyme, etc. (Fuente et al., Biochem. J. (1997) 327, 59–64).

As to *Flavobacterium lutescens* (which was re-identified from *Flavobacterium fuscum*) IFO 3084 used in bioassay of L-lysine, it is known that 2-oxoglutarate 6-aminotransferase [or lysine 6-aminotransferase (hereinafter also referred to as LAT)] catalyzing the following pathway is present (Soda et al., Biochemistry 7 (1968), 4102–4109, ibid. 4110–4119).

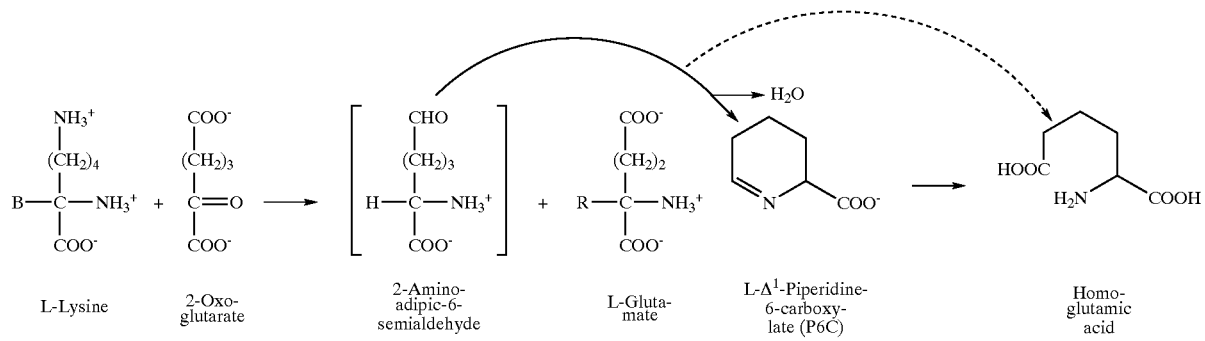

| L-Lysine | 2-Oxo-glutarate | 2-Amino-adipic-6-semialdehyde | L-Glutamate | L-Δ¹-Piperidine-6-carboxylate (P6C) | Homo-glutamic acid |

In the above bioassay, the absorbance of the product obtained by reacting piperidine-6-carboxylic acid (hereinafter, also referred to as P6C) with o-aminobenzaldehyde is measured. In another bioassay of L-lysine, the L-lysine 6-dehydrogenase activity of *Agrobacterium tumefaciens* is utilized (Misono et al., J. Biochem. (Tokyo) 105 (1989), 1002–1008).

The above IFO 3084 strain is commonly used in bioassay of L-lysine as mentioned above, and its use method is also established. Therefore, if the IFO 3084 strain had a gene encoding a protein having P6C (or, the 2-aminoadipic acid semialdehyde which is said to be in a quantitatively equilibrium state with P6C in a living body) dehydrogenase (hereinafter, also merely referred to as dehydrogenase) activity, in addition to LAT, the strain would be a candidate bacterium for gene cloning meeting the object of the present invention, namely the object to provide a gene participating in the production of homoglutamic acid.

SUMMARY OF THE INVENTION

The present inventors have tried cloning of the lysine-6-aminotransferase (LAT) gene (lat) of *Flavobacterium lutescens* and, according to circumstances, a gene encoding a protein having dehydrogenase activity on P6C of the bacterium. However, as cloning methods regularly used for such a case, a method of obtaining a targeted gene from DNA consensus sequences between amino-transferases of other bacteria, and a method utilizing information obtained from the result of amino acid sequencing of a purified protein, and the like have all failed in their early researches.

However, unexpectedly, they have found that when the host-vector system finally selected by the inventor is used, a gene at least capable of participating in the production of homoglutamic acid, more specifically a gene encoding a protein having dehydrogenase activity on P6C can be cloned by shotgun cloning. They have also found that a modifier having a certain homology (or identity) to the gene also functions similarly.

On the other hand, the above Soda et al., Biochemistry 7 (1968), 4110–4119 discloses a process of obtaining crystalline LAT of a molecular weight of 116,000 from *Achromobactor liquidum* (=*Flavobacterium lutescence*), and Yagi et al., J. Biochem. 87 (1980), 1395–1402 discloses that LAT from *Flavobacterium lutescens* is composed of four non-identical subunits of A, B1, B2 and C. Their early researches of cloning a gene encoding a protein having LAT activity utilizing the information obtained from the amino acid sequencing of the purified LAT protein, based on these descriptions, have failed. However, using a process entirely different from the processes described in these prior art references, the present inventors have purified proteins having LAT activity from *Flavobacterium lutescens*, have determined the amino acid sequences of the obtained proteins, and have cloned the objective genes utilizing these sequence informations, and as a result they have succeeded in cloning a gene encoding LAT (lat). The invention is based on the above findings.

Thus, according to the invention is provided an isolated pure DNA containing a gene participating in the production of homoglutamic acid which gene can be obtained from a bacterium belonging to the genus *Flavobacterium lutescens*, or a modifier which hybridizes with the gene under a stringent condition and has a function capable of recovering the homoglutamic acid-producing ability of a mutant which lacks the producing ability.

More specifically, the gene participating in the production of homoglutamic acid is a DNA encoding partly or wholly at least one protein selected from the group consisting of a protein having LAT activity and a protein having dehydrogenase activity, or a modifier thereof.

The invention also relates to an autonomously replicative or integration replicative recombinant plasmid carrying the DNA, and a transformant obtained by transformation with the recombinant plasmid, and a process of producing homoglutamic acid using the transformant.

HG and Lys show the moved position of homoglutamic acid and the moved position of L-lysine, and St; 1st pCF213, 2nd pCF213 and 3rd pCF213; Wild pCF213 and Wild pCF704; 1st pCF704 and 2nd pCF704; and 1st pCF 111 are the results of TLC analyses of homoglutamic acid standard substance; culture broths of the first, the second and the third mutants having pCF 213, respectively; culture broths of wild type strains having pCF 213 and pCF 704, respectively; culture broths of the first and second mutants having pCF 704, respectively; and culture broths of the first mutant having pCF 111; respectively.

Figure 4:
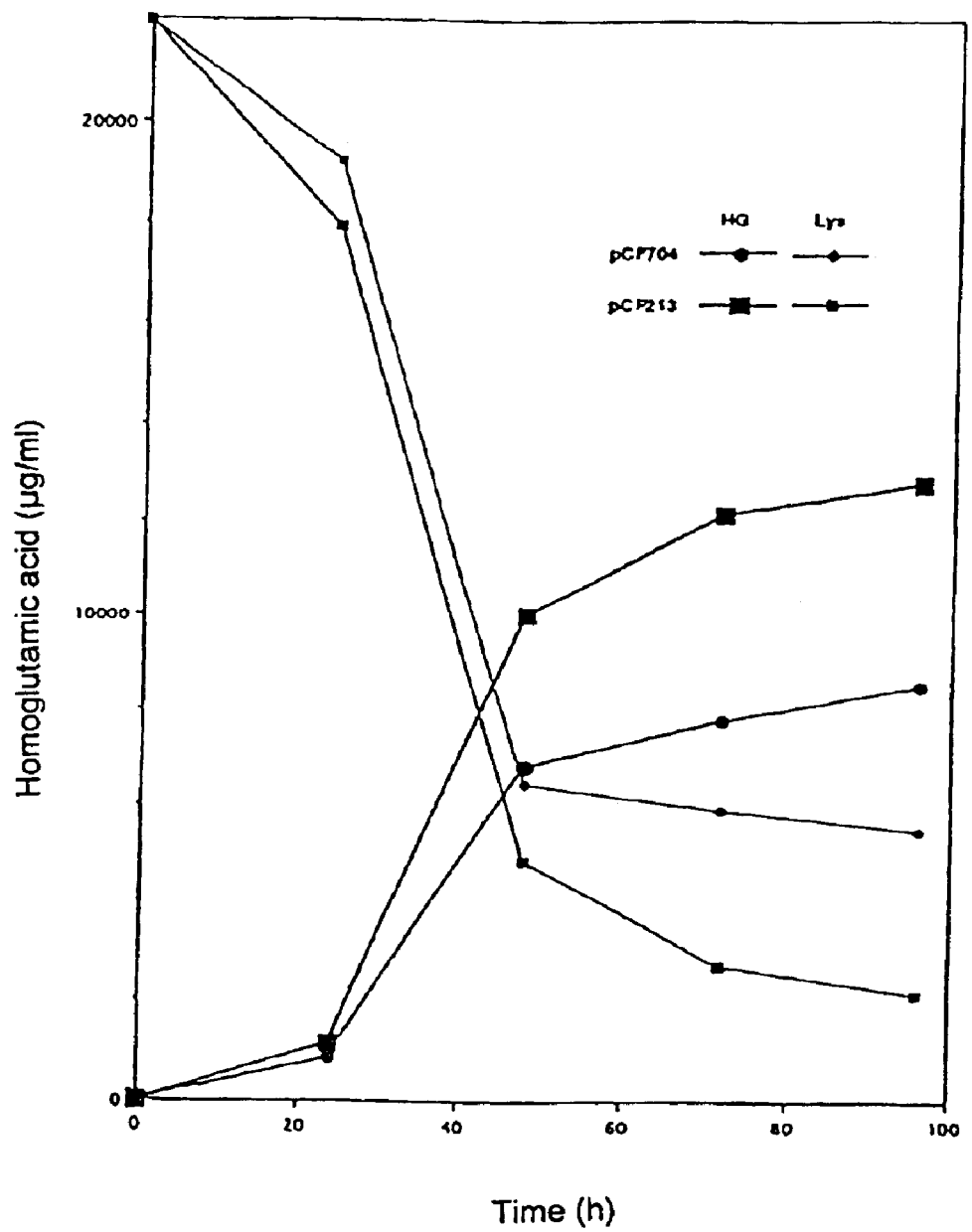

FIG. 4 is a graph showing the productivity of homoglutamic acid with time lapse of *F. lutescens* IFO 3084 (pCF213) (in the drawing, represented by pCF213) and *F. lutescens* IFO 3084 (pCF704) (in the drawing, represented by pCF704).

Figure 5:
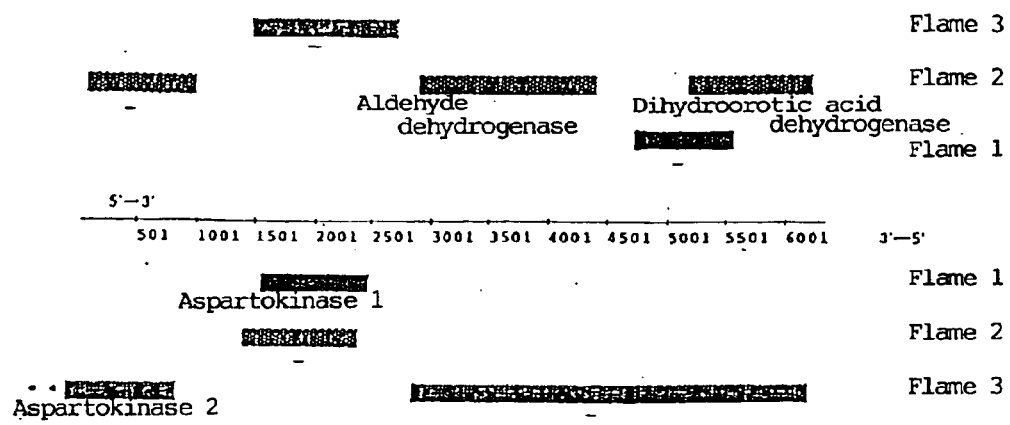

FIG. 5 is a graph showing the presence position ORF found based on the base sequence of the pCF213 insert region.

Figure 6:
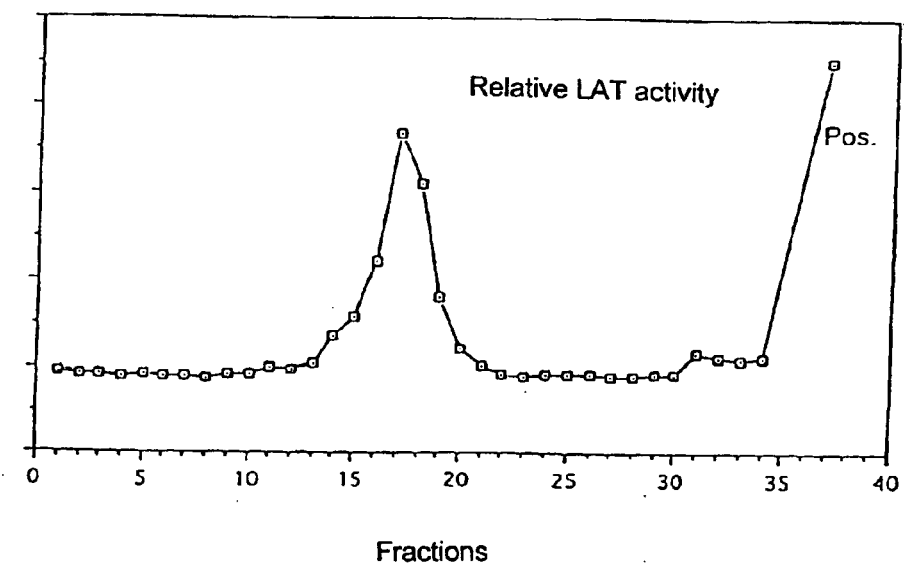

FIG. 6 is a graph showing relations between the elution fractions by the MonoQ HR5/5 column treatment in 3(6) of Example 2 and the relative LAT activities.

Figure 7:
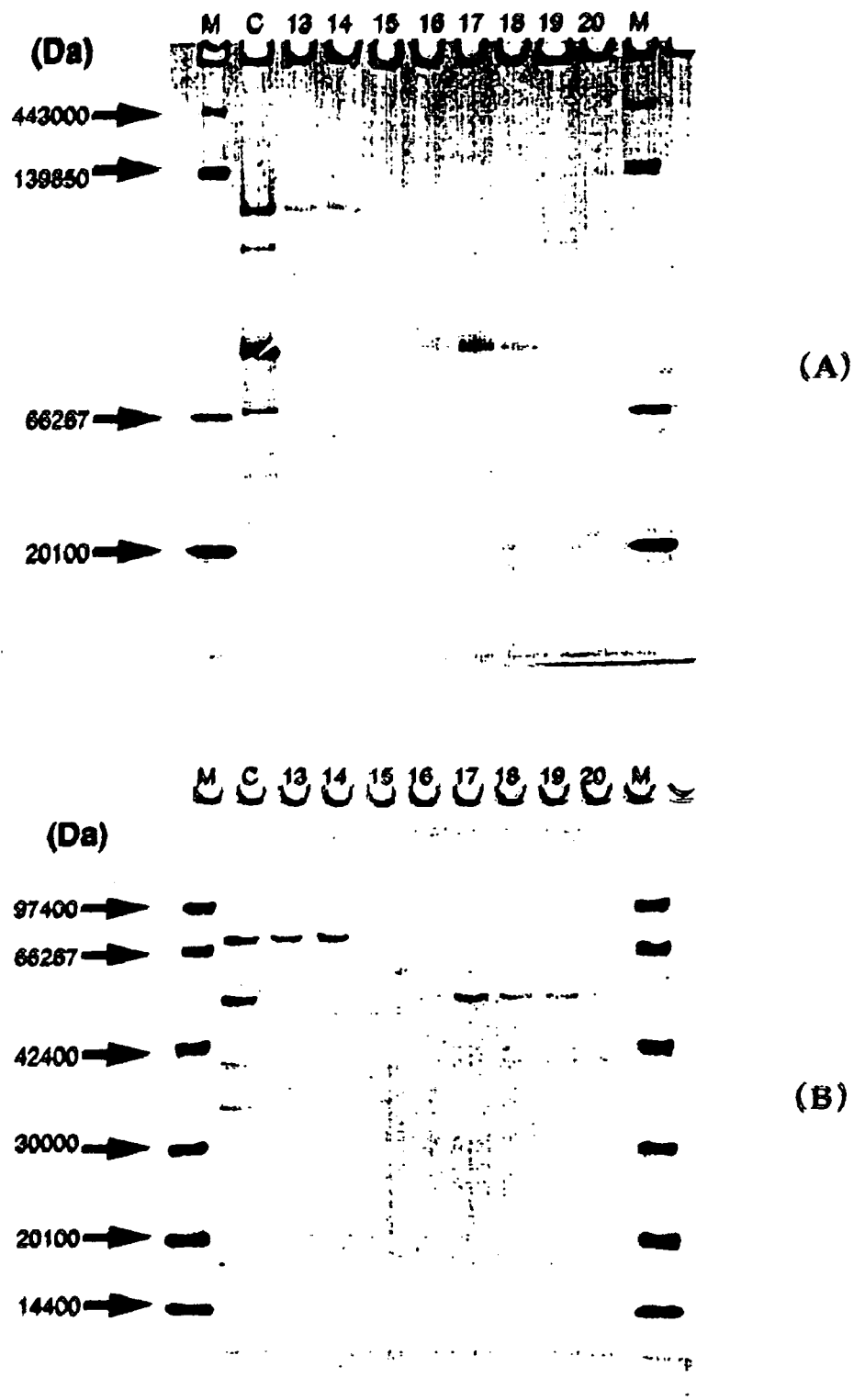

FIG. 7 is a photograph in place of a drawing showing the results of Native PAGE (A) and SDS-PAGE (B) of the LAT active fractions using Multigel 4/20 and 10/20, in 3(7) of Example 2. In the drawing, M is a molecular weight marker, C represents the ultra-filtrate obtained in 3 (5) of Example 2, and the figures represent the respective fraction numbers.

Figure 8:
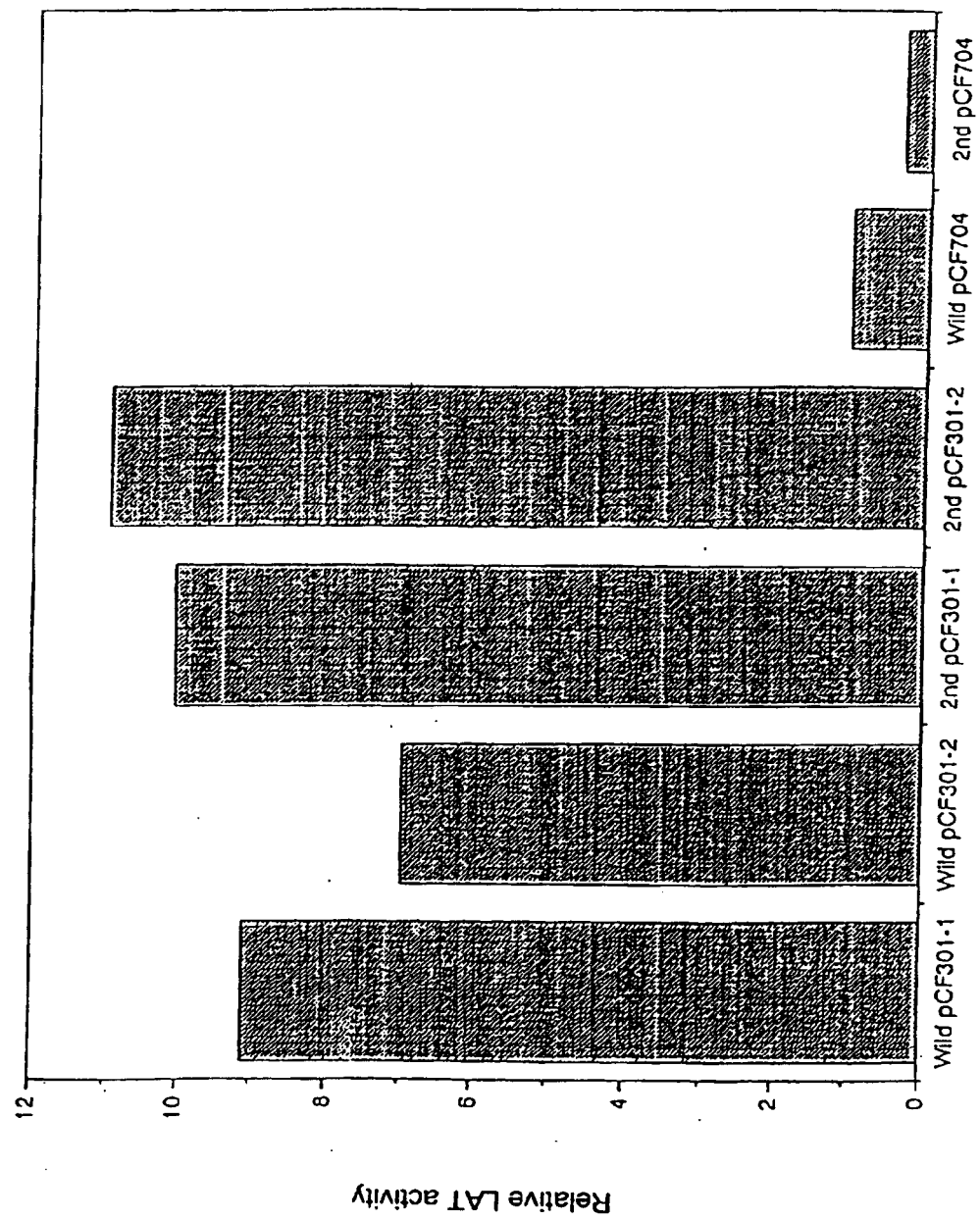

FIG. 8 is a graph showing relative LAT activities in homoglutamic acid productivity-lacking mutants and wild type strains by various plasmids.

Figure 9:
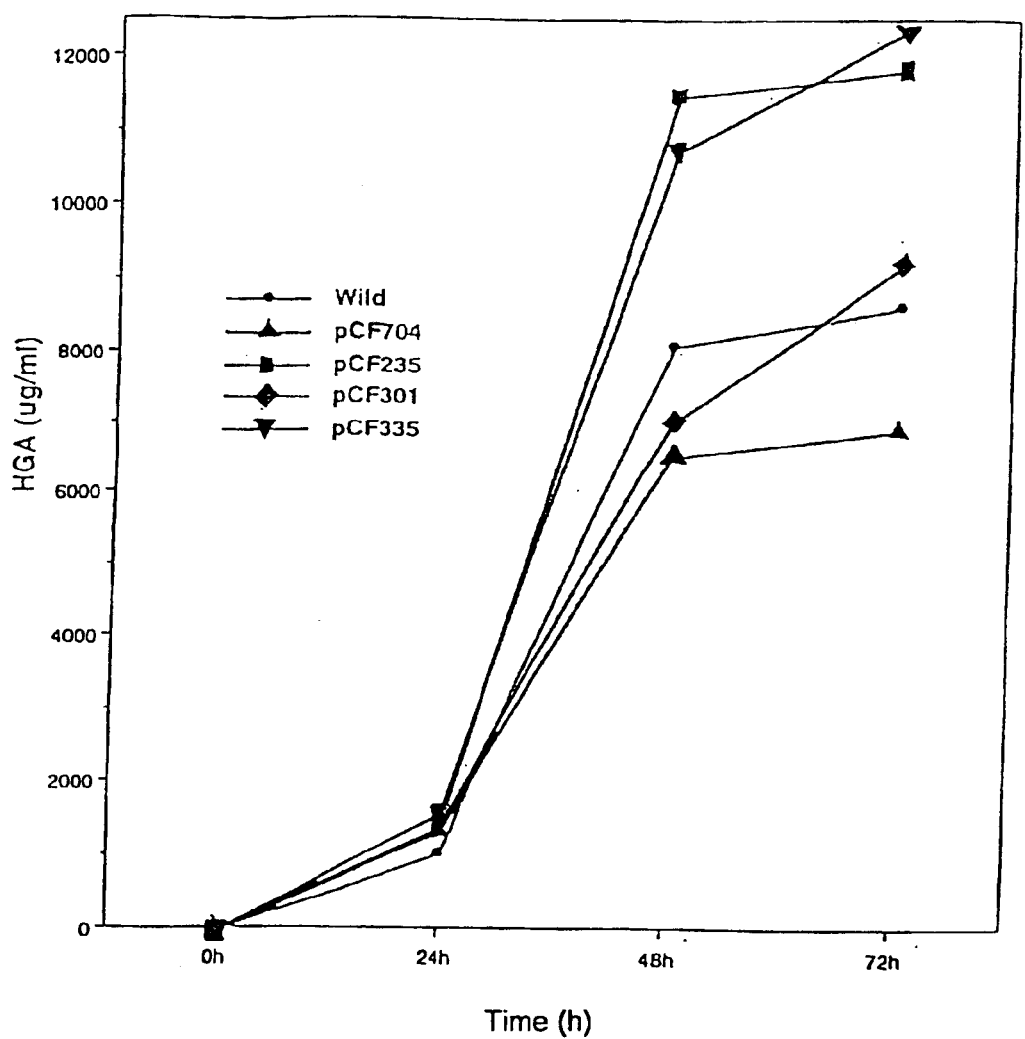

FIG. 9 is a graph showing the productivity of homoglutamic acid with time lapse of *F. lutescens* IFO 3084 transformed with various plasmids.

DESCRIPTION OF THE PREFERRED EMBODIMENTS

As to origins of genes according to the invention, any strains of *Flavobacterium lutescens* (hereinafter, also referred to as *F. lutescens*) including spontaneous mutants so long as they can provide a gene participating in the production of homoglutamic acid which gene can be expressed, for example, in *F. lutescens* as a host. However, mentioned as preferred is the IFO 3084 strain which is easy to obtain and whose suitable handling conditions such as culture are established.

The gene participating in the production of homoglutamic acid in the invention means any gene capable of participating in the two-stage conversion system from L-lysine to homoglutamic acid via P6C or 2-aminoadipic acid-6-semialdehyde which is chemically in an equilibrium relation with P6C (the former stage: LAT activity, the latter stage: dehydrogenase activity). First of all, as specific examples of genes encoding a protein having dehydrogenase activity which is the latter conversion system, there can be mentioned genes which can be obtained using the host-vector system established by the present inventors based on the following strategy.

Establishment of a suitable host-vector system of *F. lutescens* is necessary for carrying out the gene manipulation of *F. lutescens*, but therefor it is needed to solve the following three problems.

(1) Obtain a replicon which can autonomously replicate in *F. lutescens*.
(2) Obtain a drug resistance marker which can be expressed and function in *F. lutescens*.
(3) Establish a method of introducing a DNA into *F. lutescens*.

Fortunately, the above problems (1) and (2) could be solved by finding that pBBR122, lately put on the market by Mo Bi Tec corporation, which autonomously replicates in a wide range of Gram-negative bacteria and has kanamycin and chloramphenicol resistance can be used. For solution of the above problem (3), first, it becomes a prerequisite that a method of introducing the plasmid pBBR122 into *F. lutescens* is established. However, examination was made based on the method of DNA introduction into *E. coli* by the electroporation method, as a result a colony of *F. lutescens* grew in an L plate containing 20 μg/ml kanamycin, and by liquid culturing this and extracting plasmids by the alkali SDS method, it was confirmed that pBBR122 was stably held in *F. lutescens*. Thus, the problem (3) was also solved. As to this host-vector system, it has itself been known that when other bacteria were used as a host, (a) transformation efficiency is very high and (b) a DNA fragment of a suitable size can be inserted into pBBR122 (J. Bac. 178 (1996), 1053–1060), but it was revealed that the above (a) and (b) are possible also in *F. lutescens*, and further it was made possible to amplify the obtained gene in *F. lutescens*, and more over, it was also made possible to obtain a gene encoding a protein having dehydrogenase activity on P6C by shotgun cloning. For facilitating the operation, pCF704 in which the multicloning site of pUC19 was introduced in place of the chloramphenicol resistance gene of pBBR122 was prepared, and this was then used as a vector.

Then, in order to establish a system for evaluating an obtained and amplified gene, mutation was induced in *F. lutescens* IFO 3084 with N-methyl-N'-nitro-N-nitrosoguanidine (NTG), and screening was made using an MEM plate (pH 7.0) containing eosin Y.

Thus, the first mutant not producing homoglutamic acid at all, and the second and third mutants only slightly producing homoglutamic acid were obtained. In the first mutant not producing homoglutamic acid at all, lat activity equal to the wild type strain was confirmed, and in the second and third mutants only slightly producing homoglutamic acid, only slight lat activity was confirmed. Namely, there is a possibility that the first mutant is suffering some injuries to gene(s) other than lat participating in the production of homoglutamic acid, and on the other hand the second and third mutants are suffering some injuries at least to lat.

Then, the genome DNA of the wild type strain was partly digested with SauIIIAI, and the 6–8 kbp fragments were inserted into the BamHI site of pCF704, respectively, to prepare a DNA library. These plasmids were introduced into the first, second and third mutants, respectively, and strains which recovered homoglutamic acid-producing ability were screened. In this occasion, a method was used which comprises collecting colonies blackened in a MEM plate (pH 7.0) containing eosin Y, used for the screening of the mutants, and confirming homoglutamic acid-producing ability thereof by TLC. As representable ones of these mutants, the second mutant (*Flavobacterium lutescens* 2nd mutant) was deposited on Jul. 6, 1998 with National Institute of Bioscience and Human Technology, Agency of Industrial Science and Technology, and has been assigned an accession number of FERM P-16874, and the first mutant (*Flavobacterium lutescens* 1st mutant) was deposited on Jun. 10, 1999 with the Institute, and has been assigned an accession number of FERM P-17419, and these strains are kept there. These FERM P-16874 strain and FERM P-17419 strain were transferred on Jul. 26, 1999 on their deposition to the international deposition authority on Budapest Treaty in the Institute, and have been assigned accession numbers of FERM BP-6798 and FERM BP-6799, respectively.

As a result, a strain having a plsmid complementing the productivity of homoglutamic acid of the first mutant and a strain having a plsmid partly complementing the productivity of homoglutamic acid of the second mutant were obtained. However, the plasmids of these strains, particularly plasmid of the strain complementing the second mutant were liable to be deleted, and further screening for obtaining a stable plasmid has been needed. As a result of DNA fragment analysis with restriction enzyme treatment, it was revealed that the thus obtained plasmid designated pCF111 which complements the first mutant and partly complements the second mutant and the plasmid designated pCF213 were apparently quite the same plasmid.

On the other hand, pCF111 and pCF213 were re-transformed into the first, second and third mutants, respectively, and homoglutamic acid-producing ability was checked. As a result, both plasmids complemented the first mutant, but only partly complemented the second and third mutant.

Based on the complementation test, it was revealed that in a plasmid sufficiently recovering the homoglutamic acid-producing ability of a homoglutamic acid productivity-lacking mutant, a gene participating at least in the production of homoglutamic acid, more specifically some gene other than lat is present.

Thus, not limited thereto, but as one of the "genes participating in the production of homoglutamic acid", there can be mentioned a gene which is contained in the insert part of plasmid pCF213 and encoding a protein having dehydrogenase activity. For example, this gene is present in the sequence shown in SEQ ID NO: 2, and the protein encoded thereby is shown in SEQ ID NO: 10.

On the other hand, a gene participating in the former conversion, namely encoding a protein having LAT activity according to the invention can be cloned as follows.

*F. lutescens* is cultured under a certain culture condition, the obtained strain is fractured, the fracture dispersion is centrifuged to remove the fractured cells, and from the thus obtained cell extract, the desired protein is isolated and purified by ultracentrifugaztion treatment, ammonium sulfate precipitation, desalting, ion exchange column chromatography, affinity column chromatography, ultrafiltration, electrophoresis, etc.

From the analytical results of the N-terminus amino acid sequence of the purified protein, DNA primers are designed, and PCR is carried out on the genome DNA of *F. lutescens* (IFO 3084) strain. Based on the DNA fragment amplified by PCR further PCR is carried out, and thereby the neiborhood region of both outer sides of the DNA fragment is obtained. Thus, a DNA encoding the desired protein of the invention is obtained.

Thus, it becomes possible to provide a DNA encoding a protein having LAT activity as another gene participating in the production of L-homoglutamic acid. Namely, as another gene of the invention, there can, for example, be mentioned one having a sequence composing the coding region of the base sequence of SEQ ID NO: 1. The N-terminus of the corresponding purified protein is Ser as shown in SEQ ID NO: 1, but it is considered that N-terminal Met is processed after translation.

Further, the DNA containing a gene participating in the production of homoglutamic acid according to the invention includes a DNA containing at least one each of the gene encoding a protein having dehydrogenase activity and the gene encoding a protein having LAT activity.

In addition, the gene referred to in the invention also includes a modifier of both above genes which has a base sequence hybridizing with one of both genes under a certain hybridization condition, for example, under a stringent condition, at 60° C. in 2×SSC (in standard citic acid saline), preferably at 60° C. in 0.5×SSC, particularly preferably at 60° C. in 0.2×SSC, and has a function capable of recovering the homoglutamic acid-producing ability of a mutant of *F. lutescens* lacking the producing ability.

More specifically, a modifier of a gene encoding a protein having dehydrogenase activity is one showing at least 70% of identity with the base sequence of from base 2855 to base 4387 in SEQ ID NO: 2, and a modifier of a gene encoding a protein having LAT activity is one showing at least 50%, preferably 70%, more preferably 95% of identity with the base sequence of from base 545 to base 2658 (coding region) in SEQ ID NO: 1.

Such modifiers include one wherein base(s) is/are removed or added or part of the bases is replaced with other base(s), at the 5'-terminus or 3'-terminus or halfway of one of both the above sequences. The modifier wherein part of the bases is replaced with other base(s) also includes a modifier which encodes the same protein but has a base sequence different from those of both the above genes because of degeneracy of genetic code.

It is recommended to make the substitution of base other than substitution followed by degeneracy of genetic code, considering estimated amino acid sequences encoded by both the above genes, so as to have a similar shape as the whole of protein, based on similarity of the side chain of each amino acid, for example hydrophobicity, hydrophilicity, charge, size, etc. Thus, a modifier having a function equal to the function of one of both the above genes, namely a function capable of recovering the homoglutamic acid-producing ability of a mutant of *F. lutescens* which lacks the producing ability will be obtained in a considerably high probability.

The modifier according to the invention can be synthesized using a nucleic acid synthesizer or prepared by per se known point mutagenesis or site-directed mutagenesis, considering the base sequences of both the above genes or estimated amino acid sequences encoded by them.

According to the invention, a recombinant plasmid carrying the above gene or modifier can also be provided. Such a plasmid can be autonomously replicative one containing, besides the above gene or modifier, an autonomously replicative sequence, a promoter sequence, a terminator sequence, a drug resistance gene, etc. Further, the plasmid can be integration type plasmid containing a sequence homologous to a certain region of the genome of the host intended to be used. As an example of the autonomously replicative recombinant plasmid carrying a DNA containing a gene encoding a protein having dehydrogenase activity, there can be mentioned a plasmid pBBR122, or one comprising plasmid pBBR122 having inserted in a certain site thereof a multicloning site or having substituted a multicloning site for the certain site or region and having inserted the above gene or modifier using the multicloning site. As specific examples of such plasmids, there can be mentioned ones designated plasmids pCF 111 and pCF213 in the specification. pCF213 can be obtained by a per se known plasmid isolation method from *Flavobacterium lutescens* IFO 3084 (pCF213) which was deposited on Mar. 11, 1998 with National Institute of Bioscience and Human Technology, Agency of Industrial Science and Technology, and has been assigned an accession number of FERM P-16699, and then transferred to international deposition on Budapest Treaty, and has been assigned an accession number of FERM BP-6797. A recombinant plasmid carrying a DNA containing a gene encoding a protein having LAT activity and a recombinant plasmid carrying a DNA containing both genes can also be constructed in the same manner as in the pCF213.

According to the invention, there can further also be provided a transformant obtained by transforming a bacterium belonging to the genus *Flavobacterium* as a host with the above recombinant plasmid. As the host bacterium belonging to the genus *Flavobacterium*, any strain of any species can be used so long as it meets the object of the invention, but as preferred ones, there can be mentioned *F. lutescens* IFO 3084 and *F. lutescens* SP.7-1 (FERM BP-5457).

Thus, as a specific example of the above transformant, there can be mentioned one obtained by transforming *F. lutescens* IFO 3084 or *F. lutescens* SP.7-1 with pCF213, and *F. lutescens* IFO 3084 (pCF213) is deposited as the FERM BP-6797 with the international deposition authority of National Institute of Bioscience and Human Technology.

According to the invention, a process of producing homoglutamic acid using the transformant is also provided. In the process, the transformant in a medium grown by culture is contacted with L-lysine or in some case P6C (or 2-aminoadipic 6-semialdehyde) as a starting material, or the starting material is contacted with a grown transformant or treated cells thereof (e.g., cells treated with an organic solvent, a cell extract, immobilized treated cells) to convert the starting material to homoglutamic acid.

As carbon sources of the medium, any carbon sources can be used so long as they are utilizable by the transformant, and when *F. lutescens* is used as a host, there can, for example, be used saccharides such as glucose, fructose, sucrose and dextrin, sugar alcohols such as glycerol and sorbitol, and organic acids such as fumaric acid and citric acid, and it is desirable that the addition amount of these carbon sources is, usually, on the order of 0.1 to 10% by weight (hereinafter, abbreviated as %).

As nitrogen sources of the medium, there can, for example, be used ammonium salts of inorganic acids such as ammonium chloride, ammonium sulfate and ammonium phosphate, ammonium salts of organic acids such as ammonium fumarate and ammonium citrate, and further natural nitrogen sources such as meat extract, yeast extract, corn steep liquor and casein hydrolyzate, and it is desirable that the addition amount of these nitrogen sources is, usually, on the order of 0.1 to 10%.

As inorganic salts, there can, for example, be used alkaline metal salts of phosphoric acid such as potassium phosphate and sodium phosphate, alkaline metal chlorides such as potassium chloride and sodium chloride, and metal salts of sulfuric acid such as magnesium sulfate and ferrous sulfate, and it is desirable that the addition amount of these inorganic salts is, usually, on the order of 0.001 to 1%.

Among them, liquid culture using a usual growth medium for bacteria is preferred, and glucose, maltose, starch, etc., as carbon sources and ammonium sulfate, peptone, yeast extract, soybean meal, etc., as nitrogen sources are particularly effective. In addition, potassium phosphate, magnesium sulfate, table salt, etc., are usually used as inorganic salts.

It is recommended that the culture of the microorganism is carried out in such a medium at 20 to 40° C., preferably 28 to 37° C. and at a pH of 5 to 9, preferably 6 to 8 under an aerobic condition.

The contact during the culture of the grown transformant with the starting material is carried out by previously adding the starting material in the medium or appropriately adding the starting material during the culture. The contact can also be carried out, after completion of the culture, by stirring or shaking the collected cells or treated cells and the starting material in a medium or a suitable buffer, if necessary with addition of suitable coenzymes, etc., in a reactor, or by flowing a starting material-containing matter onto immobilized cells.

The case where the transformant and L-lysine are contacted during the culture is taken as an example, and it is more specifically described below. The transformant is inoculated into a medium and cultured, for example, at 20 to 40° C. for 12 to 120 hours to obtain a cultuer broth of the strain containing 106 to 1010 microorganisms as the transformant per ml. The starting material L-lysine as a solution in water or an auxiliary solvent or L-lysine as such without being dissolved is added so that the final concentration may usually be 0.5 to 30 mg/ml, and reaction is carried out usually at 20 to 40° C. for 18 hours to 7 days, preferably 18 hours to 5 days. Then, homoglutamic acid can be obtained by ordinary purification methods, for example, various ion exchange chromatography using cation exchange resins, anion exchange resins, etc., adsorption chromatography using HP20, etc., precipitation or crystallization utilizing solvents and temperature, and the like.

The shape and addition time of L-lysine to be added is not particularly limited, but preferably L-lysine is used as monohydrochloride in view of solubility, and it can be added at the start of culture or during the culture, e.g. in 1st to 5th day.

According to the invention is provided a DNA containing a gene participating in the production of homoglutamic acid which gene converts L-lysine to homoglutamic acid. This DNA is useful in a microbiological production process of homoglutamic acid. According to the invention are also provided a process of producing homoglutamic acid by a transformant capable of producing homoglutamic acid efficiently, and its use.

Hereinafter, the invention is further detailedly described by specific examples. These specific examples are provided for facilitating the understanding of the invention, and it is not intended to restrict the invention to them.

EXAMPLE 1

Cloning of a gene encoding a protein having dehydrogenase activity, etc.

1. Obtention of a Homoglutamic Acid-Not Producing Strain

*F. lutescens* IFO 3084 strain was inoculated into 3 ml of L medium (1.0% polypeptone, 0.5% yeast extract, 0.5% NaCl, 0.1% glucose, pH 7.2), and shaking cultured at 32° C. overnight. 100 µl of the culture broth as an inoculum was inoculated into 50 ml of L medium, and shaking cultured at 32° C. for 4.5 hours. The cells were collected from this culture broth by centrifugation of 5,000×g for 10 minutes, washed once with 0.2 M phosphate buffer (pH6.0), and suspended in 6 ml of 0.2 M phosphate buffer (pH6.0). 50 µl of 80 mg/ml NTG was added to this cell suspension, and shaking culture was carried out at 32° C. for 20 minutes. Cells collected from this culture broth were washed once with 0.2 M phosphate buffer (pH 6.0), and the whole amount was inoculated into 50 ml of L medium and shaking cultured at 32° C. overnight. 500 µl portions of this culture broth were poured, respectively, 500 µl portions of 60% glycerol solution were added, and the mixtures were well mixed, respectively, and then freeze stored at −70° C. The freeze stored mixtures are referred to as mutant storage suspensions.

Figure 1:
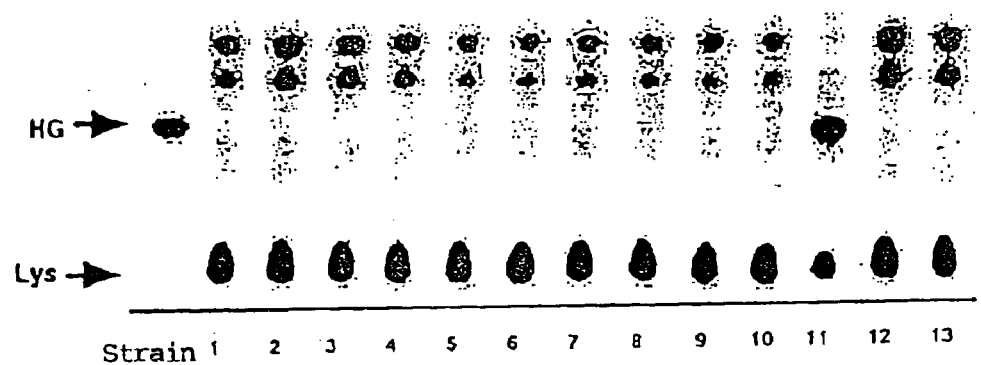
FIG. 1 is a drawing showing the analytical results by thin layer chromatography of homoglutamic acid production by mutants of *F. lutescens*. St is standard homoglutamic acid (HG), Lanes 1 to 4, Lanes 5 to 7, Lanes 8 to 10, Lane 11, and Lanes 12 and 13 show the analytical results of the first mutants, the second mutants, the third mutants, the wild type strain and the first mutants having plasmid pCF704, respectively.
Figure 2:
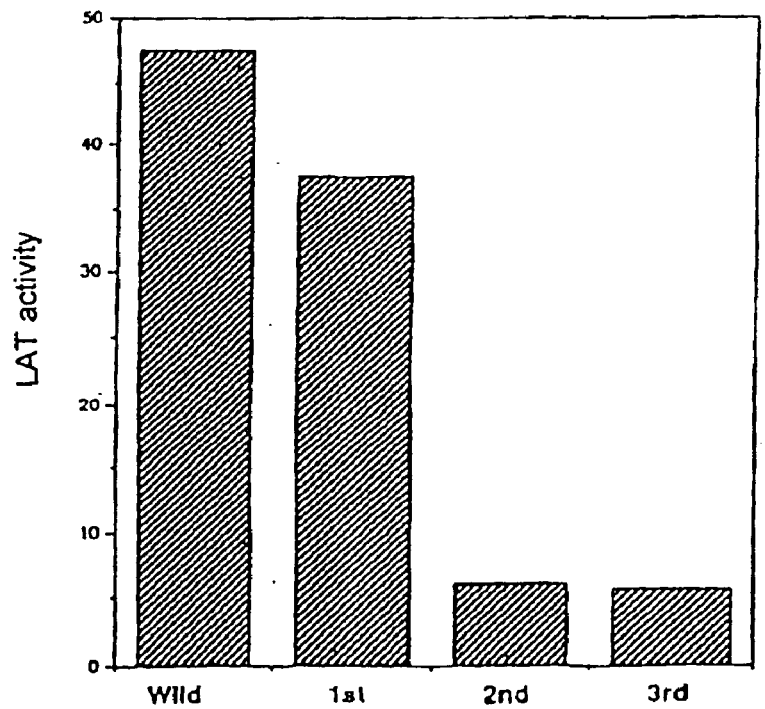
FIG. 2 is a graph showing the lysine 6-aminotransferase (LAT) activity of mutants of *F. lutescens*. Wild, 1st, 2nd and 3rd show the LAT activities of the wild type strain, the first mutant, the second mutant and the third mutant, respectively.

This mutant storage suspension was $10^6$-fold diluted with 0.85% NaCl, and 100 µl portions of the dilution were smeared on MEM agar media (0.5% polypeptone, 0.2% yeast extract, 1.0% lysine-HCl, 0.006% Methylene Blue, 0.04% eosin Y and 1.5% agar, pH 7.2) in 8-cm Petri dishes, and culture was carried out at 32° C. for 3 days. White colonies among the grown colonies were inoculated into 1 ml portions of a screening medium (1.0% polypeptone, 0.2% yeast extract, 1.0% lysine-HCl, pH 7.2), and shaking cultured at 32° C. for 2 days. 3 µl of each culture was transferred to a silica gel TLC plate, and dried. This plate was developed with a solvent system consisting of butanol, acetic acid and water (3:1:1), and subjected to ninhydrin coloring, and thereby each lane was checked for the presence or absence of homoglutamic acid. Thus, from the mutants were separated the first mutant (FERM BP-6799) not producing homoglutamic acid at all, and the second mutant (FERM BP-6798) and the third mutant producing just a bit amount of homoglutamic acid. The results obtained by checking these mutants for the ability of conversion of from L-lysine to homoglutamic acid (or productivity of homoglutamic acid) by TLC analysis are shown in FIG. 1. In FIG. 1, homoglutamic acid is represented by HG (this is also the case with other drawings). The results of assay of LAT activity on these mutants are shown in FIG. 2.

2. Construction of a Host-Vector System and a Transformation System

*F. lutescens* IFO 3084 strain was inoculated into 3 ml of L medium, and shaking cultured at 32° C. overnight. 100 µl of the culture broth as an inoculum was inoculated into 50 ml of L medium, and shaking cultured at 32° C. for 4.5 hours. The cells were collected from this culture broth by centrifugation of 5,000×g for 10 minutes, washed once with 10% glycerol solution, and suspended in 3 ml of 10% glycerol solution. 200 µl portions of this suspension were poured, and freeze stored at −70° C. The freeze stored suspensions are referred to as Electrocell storage suspensions. This storage suspension was thawed on ice, and 1 µl of a solution of 200 µg/ml of Broad Host Range Vector pBBR122 (Mo Bi Tec inorporation) in TE was added. The mixture was put in 0.2-cm Electrocuvette (BIORAD incorporation), electric pulse was once given under a condition of 2.4 kV, 200 Ω and 25 µF using Gene Pulser II (BIORAD incorporation). Then the cells were put in a Falcon tube, 1 ml of ice-cooled L medium was added, and shaking culture was carried out at 32° C. for 2 hours. The culture broth was smeared on L agar medium (1.0% polypeptone, 0.5% yeast extract, 0.5% NaCl, 0.1% glucose, 1.5% agar, pH 7.2) containing 20 µg/ml kanamycin, and cultured at 32° C. for 3 days. A transformant of a number of $2.4 \times 10^5$ was obtained.

3. Construction of a Plasmid pCF704

A primer having an EcoRI site and a primer having an NcoI site were synthesized (Pharmacia incorporation), and the muticloning site and 95 bp of its neiborhood region of pUC18 were amplified, using Taq polymerase (Pharmacia incorporation) and PCR Thermal Cycler PERSONAL (Takara company). This DNA fragment was digested with restriction enzymes EcoRI and NcoI, and the digested product was ligated to the EcoRI and NcoI sites of pBBR122 using Ligation Kit version 2 (Takara company). An *E. coli* competent cell JM109 (Takara company) was transformed with this reaction mixture, and from the resulting transformant, a plasmid pCF704 was prepared using QIAGEN Plasmid Midi Kit.

4. Construction of a Plasmid pCF213

The genome DNA of *F. lutescens* IFO 3084 strain was extracted and purified according to QIAGEN Blood and Cell Culture DNA Kit. This genome DNA was partly decomposed with a restriction enzyme SauIIIAI, and the resulting 6 to 8 kbp fragments were cut out from agarose gel, and DNAs were recovered and purified using Ultrafree C3 Unit 0.45 µm (Millipore corporation) and dissolved in TE solution. The resulting solution is referred to as Insert DNA solution. On the other hand, pCF704 was digested with a restriction enzyme BamHI, and the digest was dephosphorylated with alkaline phosphatase. The resulting digest and Insert DNA solution were subjected to ligation reaction using Ligation Kit version 2 (Takara company), and the reaction mixture was used as a DNA library.

This DNA library was added to the Electrocell storage suspension of the second mutant, and electric pulse was given. The resulting cells were put in a Falcon tube, 1 ml of ice-cooled L medium was added, and shaking culture was carried out at 32° C. for 2 hours. The whole amount of this culture broth was inoculated into 50 ml of L medium containing 20 μg/ml kanamycin, and shaking culture was carried out at 32° C. for 2 days. 500 μl portions of the culture broth were poured, respectively, and 500 μl portions of 60% glycerol solution were added and well mixed, respectively, and the mixtures were freeze stored at −70° C. The freeze stored mixtures are referred to as complementary strain storage suspensions.

Figure 3:
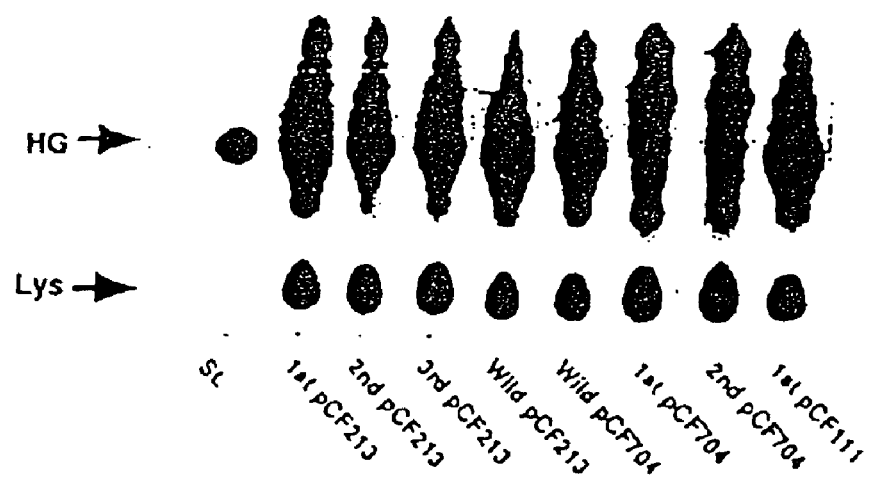
FIG. 3 shows the results of analyses by thin layer chromatography showing complementarity of homoglutamic acid productivity of homoglutamic acid productivity-lacking mutants by plasmid pCF213.

This complementary strain storage suspension was $10^3$ fold diluted with 0.85% NaCl, and 100 μl portions of the dilution were smeared on MEM agar media of pH 7.0 (0.5% polypeptone, 0.2% yeast extract, 1.0% lysine-HCl, 0.006% Methylene Blue, 0.04% eosin Y and 1.5% agar, pH 7.0) in 8-cm Petri dishes, and culture was carried out at 32° C. for 3 days. The black parts of the cells grown on the whole surfaces are referred to as complementary strain mixture cells. The respective complementary strain mixture cells were inoculated into 3 ml portions of the screening medium, and shaking cultured at 32° C. for 2 days. 3 μl portions of each of the culture broths were added dropwise on each lane of a silica gel TLC plate, and dried. This plate was developed with a solvent system consisting of butanol acetic acid and water (3:1:1), and subjected to ninhydrin coloring, and thereby each lane was checked for the presence or absence of homoglutamic acid. Thus, complementary strain mixture cells recovering homoglutamic acid-producing ability were selected and separated into single colonies, and strains recovering homoglutamic acid-producing ability were selected, and they were referred to as complementary strains. One of plasmids prepared from these complementary strains using QIAGEN Plasmid Midi KIt was named pCF213. About 6.5 kbp of an insert DNA was inserted into pCF213. Together with the complementarity of a separately obtained plasmid pCE111 on each mutant, the complementarity of the above pCF213 was examined, and the results are shown in FIG. 3.

5. Enhancement of Homoglutamic Acid-Producing Ability by pCF213

A strain obtained by transforming a wild type *F. lutescens* IFO 3084 strain with pCF704 was designated Wild pCF 704 strain, and a strain obtained by transforming a wild type *F. lutescens* IFO 3084 strain with pCF213 was designated Wild pCF 213 strain. Each of both strains was inoculated into 3 ml of the screening medium containing 20 μg/ml kanamycin, and shaking cultured at 32° C. overnight. 100 μl portions of each of the culture broths as inoculums were inoculated into 25 ml portions of a production medium (1.5% polypeptone, 0.5% yeast extract, 2.0% lysine-HCl, pH not adjusted), and shaking cultured at 32° C. for 24 hours, 48 hours and 72 hours, respectively. The supernatant of each of the culture broths were assayed for the amount of homoglutamic acid by HPLC. Namely, the culture broth was diluted with distilled water so that the total amino acid concentration got to be on the order of 1,000 mg/L, and 50 μl of the dilution was transferred to a test tube and concentrated to dryness under reduced pressure. 50 μl of a solution obtained by mixing phenyl isothiocyanate, triethylamine, ethanol and distilled water in 1:1:7:2 was added thereto, and the mixture was stirred to dissolve the residue, left alone at room temperature for 10 minutes, and concentrated to dryness under reduced pressure. The residue was dissolved in 500 μl of Solution A as the mobile phase of HPLC, and 5 μL of the solution was injected. The HPLC condition is shown below.

Column: TSK-GEL super-ODS 4.6ID×50 mm

Mobile phase:
  Solution A Mixture of a solution obtained by adjusting 140 mM sodium acetate-0.05% triethylamine to pH 6.2 with glacial acetic acid:acetonitrile in 1,000:40
  Solution B 70% acetonitrile Flow rate: 2.0 ml/min Elution condition: gradient of a fixed flow rate, linear gradient of from 2% to 40% of Solution B in from 0 to 7 minutes, 100% of Solution B in more than 7 minutes Detection: UV 254 nm Temperature: 40° C.

Under these conditions, the retention time of homoglutamic acid was 1.3 minutes, and that of lysine was 7.7 minutes.

As is seen from the results shown in FIG. 4, the wild type pCF213 strain has homoglutamic acid-producing ability 1.5 times higher than that of the wild type pCF704 strain.

6. Determination of the Gene Base Sequence of the pCF 213 Insert Region

The base sequence of the pCF 213 insert region was determined according to the primer walking method using ABIPRISM 377XL DNA Sequencer (Perkin Elmer corporation). This base sequence is shown in SEQ ID NO: 2.

The open reading frame (ORF) on the determined base sequence was determined using the method of Bibb et. al. (Gene 30, 157 (1984)). As a result, ORF shown in FIG. 5 was found.

7. Analysis of the NotI Site of About 2.5 kbp in the pCF213 Insert Region

Analysis of the NotI site of about 2.5 kbp (the base sequence of from 2077 to 4578 in SEQ ID NO: 2) in the pCF213 insert region was carried out. This NotI site of about 2.5 kbp was cut out from the agarose gel, and the DNA was recovered and purified using Ultrafree C3 Unit 0.45 μm (Millipore corporation) and dissolved in TE solution, and the termini were blunted according to DNA Blunting Kit (Takara company), and the resulting solution was referred to as Insert DNA solution. On the other hand, pCF704 was digested with a restriction enzyme HincII and then dephosphorylated with alkaline phosphatase. This and Insert DNA solution were subjected to ligation reaction using Ligation Kit version 1 (Takara company). *F. lutescens* IFO 3084 strain was transformed with this reaction mixture, and a plasmid pCF235 was prepared from the transformant using QUIAGEN Plasmid Midi Kit.

The first mutant transform with pCF235 was inoculated into 3 ml of the screening medium, and shaking cultured at 32° C. for 2 days. 3 μl portions of this culture broth were added dropwise on each lane of TLC silica gel plate and dried. This plate was developed with a solvent system consisting of butanol, acetic acid and water (3:1:1) and sujected to ninhydrin coloring, and each lane was checked for the presence or absence of homoglutamic acid. As a result, it was revealed that the first mutant transformed with pCF235 recovered homoglutamic acid-producing ability.

In the DNA sequence of about 2.5 kbp integrated into pCF235 was present an ORF encoding 510 amino acids starting from ATG of 2855th of the base sequence of SEQ ID NO: 2 and ending in TAA of 4387th. This amino acid sequence was subjected to homology search by BLAST, and as a result, showed high homology with various aldehyde dehydrogenases, and further showed high homology with the amino acid sequence of piperidine-6-carboxylic acid dehydrogenase of *Streptomyces dlavuligrus* lately registered with database (J. Bac., Vol. 180, No. 17, 4753–4756 (1998)) over the whole amino acid sequence. Taking it into account that the first mutant transformed with pCF235 recovered homoglutamic acid-producing ability and that the homoglutamic acid-producing ability of the wild type pCF213 strain was heightened, the protein encoded by this ORF can be regarded as having piperidine-6-carboxylic acid dehydrogenase.

EXAMPLE 2

Cloning of a gene encoding a protein having LAT activity, etc.

1. Assay of LAT Activity

Lysine-HCl (73 mg) and 59 mg of 2-ketoglutaric acid were dissolved in 1 ml of 0.2 M phosphate buffer (pH 7.3) containing 0.5 mM pyridoxal phosphate, and the solution was referred to as reaction solution. The reaction solution (28.75 µl) was added to 260 µl of the enzyme solution, and the mixture was left alone at 32° C. for 1 hour. 151.8 µl of a solution of 5% trichloroacetic acid in ethanol was added to discontinue the reaction, the reaction mixture was centrifuged, 90 µl of 0.2 M phosphate buffer (pH 7.3) containing 4 mM o-aminobenzaldehyde was added to 60 µl of the supernatant, and the mixture was left alone at 37° C. for 1 hour. The mixture was assayed for A465, and the fractions having relatively high A465 were referred to as LAT active fractions.

2. Culture of Strain

*F. lutescens* IFO 3084 strain was shaking cultured at 32° C. overnight. The culture broth (50 ml) as an inoculum was inoculated into 10 L of flavo-M9 medium (0.6% $Na_2HPO_4$, 0.3% $KH_2PO_4$, 0.1% $NH_4Cl$, 0.2% NaCl, 1.0% polypeptone, 0.5% yeast extract, 0.5% lysine-HCl, 0.005% silicone KM75, 0.025% $MgSO_4$, 0.0015% $CaCl_2$, pH 7.2) in 30 L jar fermenter, and aeration stirring cultured for 17 hours. The resulting culture broth (5 L) was centrifuged (1,000×g, 10 minutes) to collect the cells, and the cells were washed twice with 0.01 M phosphate buffer (pH 7.2). The cells were suspended in the same buffer and subjected to ultrasonic fracture. The fractured cells were removed by centrifugation (1,000×g, 10 minutes) to obtain a cell extract. The cell extract was ultracentrifuged (16,000×g, 90 minutes), and the supernatant fraction was subjected to the following purification operations.

3. Purification of Enzyme

All the following purification operations were carried out at 4° C., unless otherwise noted.

(1) Ammonium Sulfate Fractionation

The supernatant fraction (600 ml) obtained in Example 1 was purified by ammonium sulfate precipitation. The precipitates formed in the fractions of from 30% saturation to 80% saturation were collected by centrifugation (1,000×g, 30 minutes), and dissolved in 0.01 M phosphate buffer (pH 7.2), and the solution was dialyzed against the same buffer.

(2) Desalting

The dialyzed enzyme solution (10 ml) was poured on 4 PD10 columns (Amasham Pharmacia) and eluted and desalted with 0.1 M Tris-HCl buffer (pH 7.4) containing 0.5 mM pyridoxal phosphate.

(3) QAE-TOYOPEAL550C Column Chromatography

The desalted enzyme solution was poured on QAE-TOYOPEAL550C (TOSOH) column (φ5.5×6.0 cm) previously equilibrated with 0.1 M Tris-HCl buffer (pH 7.4) containing 0.5 mM pyridoxal phosphate, washed with the same buffer, and eluted by 2 L of sodium chloride linear gradient (0 to 1.0 M) using the same buffer, and LAT active fractions were collected.

(4) Phenyl-TOYOPERL650S Column Chromatography

1 M ammonium sulfate was added to the LAT active fractions, and the mixture was poured on Phenyl-TOYOPERL650S (TOSOH) column (φ5.5×3.0 cm) previously equilibrated with 0.01 M phosphate buffer (pH 7.2) containing 0.5 mM pyridoxal phosphate and 1 M ammonium sulfate, and eluted with 1,200 ml of ammonium 30 sulfate gradient (0.8 to 0 M) using the same buffer, and LAT active fractions were collected.

(5) Ultrafiltration

The LAT active fractions (150 ml) were ultrafiltered with ADVANTEC UP-20 to make the volume 15 ml. This concentrate (2.5 ml) was poured on PD10 column (Amasham Pharmacia), and eluted and desalted with 0.1 M Tris-HCl buffer (pH 7.4).

(6) AKTA MonoQ HR5/5 Column Chromatography

The desalted enzyme solution (3.5 ml) was poured on MonoQ HR515 column of AKTAexplorer 10S System (Amasham Pharmacia) previously equilibrated with 0.1 M Tris-HCl buffer (pH 7.4), washed with the same buffer, and eluted with 40 ml of sodium chloride linear gradient (0 to 0.4 M) using the same buffer, and LAT active fractions were collected. The LAT active fractions (5 ml) were desalted with PD10 column, and subjected to MonoQ HR5/5 column of AKTAexplorer 10S System, and LAT active fractions were collected. Relations between each fraction and relative LAT activity are shown in FIG. 6.

(7) Electrophoresis

The LAT active fractions were subjected to Multigel 4/20 and 10/20 (Daiichi Kagaku Yakuhin Co., Ltd.) and Native-PAGE and SDS-PAGE were carried out, and the results are shown in FIG. 7. As to the LAT active fractions, a band was observed at a molecular weight of around 100,000 in Native-PAGE and a band was observed at a molecular weight of around 55,000 in SDS-PAGE. A PVDF membrane was blotted with the band of a molecular weight of around 55,000 in SDS-PAGE using PhastTransfer (Amasham Pharmacia).

4. Analysis of N-Terminus Amino Acid Sequence

Analysis of N-terminus amino acid sequence of the band subjected to the blotting was carried out by Edman degradation method using HP G1005A Protein Sequencing System (HEWLETT PACKARD). As a result, it was revealed that the N-terminus amino acid sequence was

SLLAPLAPLRAHAGTRLTQG (SEQ ID NO: 7).

Based on this, DNA primers

NmaRout CCYTGIGTIARICKIGTICCIGCRT-GIGCICG (SEQ ID NO: 8).

NmaRin CCIGCRTGIGCICGIARIGGIGCIARIGGIGC (SEQ ID NO: 9).

were designed, and PCR was carried out on the genome DNA of *F. lutescens* IFO 3084 strain using LA PCR in vitro cloning KIT (Takara Company). The PCR reaction condition was 30 cycles of 94° C., 30 seconds→55° C., 2 minutes→72° C., 1 minute. As a result, a PCR amplification fragment of about 400 bp containing the above terminus and its upstream region was obtained. Based on this sequence, its neighborhood region was obtained by using PCR. Namely, the genome DNA of *F. lutescens* IFO 3084 strain was digested with restriction enzymes PstI and SalI, respectively, and the digests were subjected, respectively, to self-ligation reaction using Ligation Kit version 2 (Takara Company), and the resulting DNAs were used as template DNAs. Based on these template DNAs, DNA primers NIFout ttgatttgag cagattcgca ctgccattt (SEQ ID NO: 3)

NIRout aaggttttcg acaaagtgac catttccca (SEQ ID NO: 4)

were designed, and PCR was carried out using LA Taq (Takara Company). The PCR reaction condition was 30 cycles of 98° C., 20 seconds→68° C., 6 minutes. As a result, a PCR amplification fragment of about 2 kbp was obtained from the PstI template and a PCR amplification fragment of about 8 kbp from the SalI template. The base sequence was determined by the primer walking method using ABIPRISM 377XL DNA Sequencer (Perkin Elmer corporation) on these PCR amplification fragments. This base sequence is shown in SEQ ID NO: 1.

5. Construction of Plasmids pCF301 and pCF335

The following DNA primers wherein the PstI sites of base 545 and base 2658 of SEQ ID NO: 1 were converted to KnpI and SacI sites, respectively, ctggtaccgc tcgatccggc tctgcaccgt (SEQ ID NO: 5)

ctggagctca ggcaggtgcg ggccacgtgt (SEQ ID NO: 6)

were prepared, and PCR reaction was carried out using these primers to amplify the lat gene region. The amplified fragment of about 2.1 kbp was digested with restriction enzymes KpnI and SacI, and the resulting solution was referred to as Insert DNA solution. On the other hand, pCF704 was digested with restriction enzymes KnpI and SacI, and the digest and Insert DNA solution were subjected to ligation reaction using Ligation Kit version 2 (Takara company), and the resulting plasmid was referred to as pCF301. Further, pCF301 was digested with restriction enzymes KpnI and SacI, and the 2.1 kbp fragment was cut out from agarose gel, and this and the digest of pCF235 with restriction enzymes KpnI and SacI were subjected to ligation reaction, and the resulting plasmid was named pCF335.

6. Complementation of LAT Activity by Plasmid pCF301

A mutant obtained by transforming the second mutant with pCF704 was designated 2nd pCF704 strain, and a mutant obtained by transforming the second mutant with pCF301 was designated 2nd pCF301 strain. These strains were shaking cultured at 32° C. overnight. Each (30 µl) of the culture broths as an inoculum was inoculated into 3 ml of a production medium (1.5% polypeptone, 0.5% yeast extract, 2.0% lysine-HCL pH not adjusted) in a centrifugation tube, and aeration stirring cultured for 17 hours. The resulting culture broth (1 ml) was centrifuged (1,000×g, 10 minutes) to collect the cells, and the cells were washed with 10 ml of 0.2 M phosphate buffer (pH 7.3) containing 0.5 mM pyridoxal phosphate. The cells were suspended in 1 ml of the same buffer and ultrasonically fractured. The fractured cells were removed by centrifugation (1,000×g, 10 minutes) to obtain a cell extract. This cell extract was assayed for LAT activity. The results are shown in FIG. 8. pCF301 complemented the lat mutation in the second mutant.

7. Heightening of Homoglutamic Acid-Producing Ability by pCF335

A transformant obtained by transforming the wild type F. lutescens IFO 3084 strain with pCF704 was designated wild type pCF704 strain, and transformants obtained by transforming the IFO 3084 strain with plasmids pCF301 and pCF335 were designated wild type pCF301 strain and wild type pCF335 strain, respectively. These strains were inoculated into 3 ml portions of the screening medium containing 20 µg/ml kanamycin, respectively, and shaking cultured at 32° C. overnight. 100 µl portions of each of the culture broths as an inoculum were inoculated into 25 ml portions of a production medium (1.5% polypeptone, 0.5% yeast extract, 2.0% lysine-HCl, pH not adjusted), and shaking cultured at 32° C. for 24 hours, 48 hours and 72 hours, respectively. The amount of homoglutamic acid in the supernatant of each of the culture broths was measured by HPLC. Namely, each of the culture broths was diluted with distilled water so that the total amino acid concentration could be on the order of 1,000 mg/L, and 50 µl of the dilution was transferred into a test tube and concentrated to dryness. To the residue was added 50 µl of a mixed solution of phenyl isothiocyanate, triethylamine, ethanol and distilled water (1:1:7:2), and the mixture was stirred to make a solution, left alone at room temperature for 10 minutes and concentrated to dryness under reduced pressure. The residue was dissolved in 500 µl of Solution A as a mobile phase of HPLC, and 5 µl thereof was injected. The HPLC condition is as described in 5 of Example 1.

As a result, as shown in FIG. 9, the wild type pCF335 strain had homoglutamic acid-producing ability about twice higher than that of the wild type pcf704 strain.

What is claimed is:

1. An isolated nucleic acid sequence selected from the group consisting of:
   (a) the nucleotide sequence of SEQ ID NO: 2 encoding a protein having piperidine-6-carboxylic acid dehydrogenase activity, or a complementary strand thereof;
   (b) a nucleotide sequence encoding a protein having the amino acid sequence of SEQ ID NO: 10 which has piperidine-6-carboxylic acid dehydrogenase activity, or a complementary strand thereof;
   (c) a nucleotide sequence consisting of nucleotides 2855 to 4387 of SEQ ID NO: 2 encoding a protein having piperidine-6-carboxylic acid dehydrogenase activity, or a complementary strand thereof;
   (d) a nucleotide sequence consisting of nucleotides 2077 to 4578 of SEQ ID NO: 2 encoding a protein having piperidine-6-carboxylic acid dehydrogenase activity, or a complementary strand thereof;
   (e) a nucleotide sequence which has at least 95% homology with the nucleotide sequence of (c) encoding a protein having piperidine-6-carboxylic acid dehydrogenase activity, or a complementary strand thereof;
   (f) a fragment of nucleotide sequence (a) or (b) encoding a protein having piperidine-6-carboxylic acid dehydrogenase activity, or a complementary strand thereof; and
   (g) a nucleotide sequence which hybridizes under stringent conditions at 60° C. in 2×SSC to sequence (a), (b), (c), (d), (e) or (f) and encodes a protein having piperidine-6-carboxylic acid dehydrogenase activity.

2. The isolated nucleotide sequence according to claim 1, which is the nucleic acid sequence of SEQ ID NO: 2 encoding a protein having piperidine-6-carboxylic acid dehydrogenase activity, or a complementary strand thereof.

3. The isolated nucleotide sequence according to claim 1, which is the nucleotide sequence encoding a protein having the amino acid sequence of SEQ ID NO: 10 which has piperidine-6-carboxylic acid dehydrogenase activity, or a complementary strand thereof.

4. The isolated nucleotide sequence according to claim 1, which is the nucleotide sequence consisting of nucleotides 2855 to 4387 of SEQ ID NO: 2 encoding a protein having piperidine-6-carboxylic acid dehydrogenase activity, or a complementary strand thereof.

5. The isolated nucleotide sequence according to claim 1, which is the nucleotide sequence consisting of nucleotides 2077 to 4578 of SEQ ID NO: 2 encoding a protein having piperidine-6-carboxylic acid dehydrogenase activity, or a complementary strand thereof.

6. The isolated nucleotide sequence according to claim 1, which is the nucleotide sequence which has at least 95% homology with the nucleotide sequence of (c) encoding a protein having piperidine-6-carboxylic acid dehydrogenase activity, or a complementary strand thereof.

7. The isolated nucleotide sequence according to claim 1, which is the fragment of nucleotide sequence (a) or (b) encoding a protein having piperidine-6-carboxylic acid dehydrogenase activity, or a complementary strand thereof.

8. The isolated nucleotide sequence according to claim 1, which is the nucleotide sequence which hybridizes under stringent conditions at 60° C. in 2×SSC to sequence (a), (b), (c), (d), (e) or (f) and encodes a protein having piperidine-6-carboxylic acid dehydrogenase activity.

9. The isolated nucleotide sequence according to claim 1, which is obtained from a bacterium belonging to *Flavobacterium lutescens*.

10. A nucleic acid construct comprising the nucleic acid sequence according to claim 1.

11. The nucleic acid construct according to claim 10, which is contained in *Flavobacterium lutescens* IFO 3084 (pCF213) deposited under accession number FERM BP-6797.

12. A host cell comprising the nucleic acid construct according to claim 10, wherein the nucleic acid sequence encodes a protein having piperidine-6-carboxylic acid dehydrogenase activity.

13. A process for producing L-homoglutamic acid, which comprises culturing the host cell according to claim 12 under suitable conditions to produce the protein in the presence of 1-piperidine-6-carboxylic acid, and recovering L-homoglutamic acid.

14. The process according to claim 13, wherein the host cell is a bacterium belonging to the genus *Flavobacterium*.

15. The process according to claim 13, wherein the host cell is *Flavobacterium lutescens* IFO 3084 (pCF213) deposited under accession number FERM BP-6797.

* * * * *